United States Patent [19]
Kobayashi et al.

[11] Patent Number: 5,972,929
[45] Date of Patent: Oct. 26, 1999

[54] QUINAZOLINONE DERIVATIVE, HAIR GROWTH PROMOTER AND EXTERNAL COMPOSITION FOR SKIN USING THE SAME

[75] Inventors: Koji Kobayashi; Hirotada Fukunishi; Tsunao Magara, all of Kanagawa, Japan

[73] Assignee: Shiseido Co., Ltd., Tokyo, Japan

[21] Appl. No.: 09/137,148

[22] Filed: Aug. 20, 1998

[30] Foreign Application Priority Data

Aug. 21, 1997 [JP] Japan ................................ 9-240362

[51] Int. Cl.[6] ..................... A61K 31/495; C07D 239/90
[52] U.S. Cl. ..................... 514/212; 514/234.5; 514/259; 540/600; 544/259; 544/287; 544/119; 544/289
[58] Field of Search ..................... 544/289, 287, 544/119; 514/259, 234.5, 212; 540/600

[56] References Cited

U.S. PATENT DOCUMENTS

| | | | |
|---|---|---|---|
| 2,408,633 | 10/1946 | Guenther et al. | 260/251 |
| 3,558,610 | 1/1971 | Breuer et al. | 260/240 |
| 4,710,502 | 12/1987 | Wright . | |
| 4,753,944 | 6/1988 | Wright . | |
| 5,093,364 | 3/1992 | Richards et al. | 514/533 |
| 5,756,502 | 5/1998 | Padia | 514/248 |
| 5,763,608 | 6/1998 | Bhattacharya et al. | 544/319 |

FOREIGN PATENT DOCUMENTS

| | | | |
|---|---|---|---|
| 0 169 537 | 1/1986 | European Pat. Off. | C07D 239/90 |
| 35 123 | 2/1965 | Germany . | |
| 20 27 645 | 12/1971 | Germany | C07D 51/48 |
| 63-316778 | 12/1988 | Japan | C07D 403/04 |
| 04253904 | 9/1992 | Japan | A61K 7/06 |
| 7-304736 | 11/1995 | Japan | C07D 209/08 |
| 7-316022 | 12/1995 | Japan | A61K 7/06 |
| 7-316023 | 12/1995 | Japan | A61K 7/06 |
| 8-20521 | 1/1996 | Japan | A61K 7/48 |
| 8-26942 | 1/1996 | Japan | A61K 7/06 |
| 2 197 589 | 5/1988 | United Kingdom | A61K 7/06 |
| 95/19169 | 7/1995 | WIPO | A61K 31/42 |
| 97 10221 | 3/1997 | WIPO | C07D 239/88 |
| 98 26664 | 6/1998 | WIPO | A01N 43/54 |

OTHER PUBLICATIONS

Hamad, et al. "Some Reactions of 2–(α–Naphthyl Methyl)–(4H)–3,1 Benzoxazin–4–One", Pakistan Journal of Scientific and Industrial Research, vol. 36, No. 6–7, pp. 228–231. Jun.–Jul. 1993.

Database WPI, Week 9550, Derwent Publications, Ltd. London, GB, AN 95–385642, XP002089827 JP 07 258224 A (Daiichi Pharm. Co., Ltd.) Oct. 9, 1995.

Soc. Chimique Buzas, A., et al. Derives Pharmacologiquement actifs des quinazolonge–4 substitues en –3 Memoires Presentes A La Societe Chimique, 5e Serie pp. 1889–1891 (esp. Compound No. 10–13 and 15–16) 1959.

J Ind Chem Soc Singh, P Study in Nitrogen Mustards. Part II: Synthesis of Some 2–Alkyl–3–aryl–4(3H)–quinazolinone Derivatives as Possible Antitumour Agents, vol.LV, Aug. 1978 (pp. 801–805).

Bull Soc Chim Fr N°.333—Composes Sulfures Heterocycliques. 81—Aminoakyl–3 3 H–quinzaolinones–4, 1976 N°. 11–12 (pp. 1853–1856 —esp. Table III).

Ind. J. of Chem Seth, M Syntheses of 2–Substituted & 2,3 Disubstituted 4(3H)–Quinazolones, vol. 14B, Jul. 1976 (pp. 536–540).

Ind J of Pharm Joshi, LD Inhibition of Rat Brain Acetylcholinesterase by Substituted Quinazolones, vol. 33, No. 5 (pp. 80–82) 1961.

J Prakt Chem Klosa, V Synthese von 2,3–substituierten Chinazolon–(4)–derivaten mit Hilfe von Phosphoroxychlorid, 4 Riche, Band 14, 1961 (pp. 84–98—esp. Compound No.49–53).

*Primary Examiner*—Richard L. Raymond
*Assistant Examiner*—Ann Razgunas
*Attorney, Agent, or Firm*—Snider & Chao, LLP; Fei-Fei Chao; Ronald R. Snider

[57] ABSTRACT

A quinazolinone derivative or a salt thereof expressed by the following Formula (I);

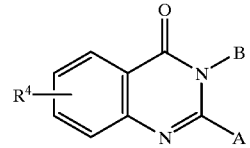

Formula (I)

wherein each of A and B is $R^1$ or $-(CH_2)_n-NR^2R^3$; wherein $R^1$ represents a hydrocarbon group of $C_{10-30}$; wherein $R^2$ and $R^3$ individually represent a hydrogen atom, a lower alkyl group, a phenyl group, or a benzyl group, or together represent a heterocyclic ring having 3–7 members; and n represents an integer of 1–5; wherein when A is $R^1$, B is $-(CH_2)_n-NR^2R^3$ and when A is $-(CH_2)_n-NR^2R^3$, B is $R^1$; and wherein $R^4$ is selected from the group consisting of a hydrogen atom, a halogen atom, a lower alkyl group, a lower acyl group, a nitro group, a cyano group, an amino group, a lower alkoxycarbonyl group, a lower alkylamino group, a lower alkoxy group, a lower acyloxy group, a carbamoyl group, a lower alkylcarbamoyl group, and a lower acylamino group. The quinazolinone derivative or the salt thereof has excellent hair growth and regrowth promoting effects, which are useful for care, improvement or prevention of hair loss in mammals and, in particular, in humans.

12 Claims, 4 Drawing Sheets

Reaction Formula AA

Reaction Formula AB

Reaction Formula AC

Reaction Formula AD

Reaction Formula AE

Reaction Formula AF

Reaction Formula BA

Reaction Formula BB

Reaction Formula BC

Reaction Formula BD

Reaction Formula BE

Reaction Formula BF

Reaction Formula BG

QUINAZOLINONE DERIVATIVE, HAIR GROWTH PROMOTER AND EXTERNAL COMPOSITION FOR SKIN USING THE SAME

RELATED APPLICATIONS

This application claims the priority of Japanese Patent Application No. 9-240362 filed on Aug. 21, 1997, which is incorporated herein by reference.

FIELD OF THE INVENTION

The present invention relates to a novel quinazolinone derivative and, in particular, to a quinazolinone derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, generation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin $B_6$.

In addition to these drugs, salicylic acid, resorcine and the like that have corneocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acid, vitamin, extract of crude drugs and the like can be compounded so as to aliment to hair follicle and activate enzyme activity.

Meanwhile, for example, D (L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain quinazolinone derivative and its salt have excellent hair growth and regrowth promoting effect, thereby accomplishing the present invention.

Namely, a quinazolinone derivative or a salt thereof in accordance with the present invention is expressed by the following Formula (I):

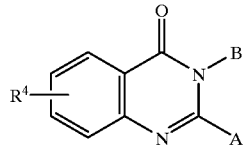

Formula (I)

wherein each of A and B is $R^1$ or $-(CH_2)_n-NR^2R^3$;
wherein $R^1$ represents a hydrocarbon group of $C_{10-30}$;
wherein $R^2$ and $R^3$ individually represent a hydrogen atom, a lower alkyl group, a phenyl group, or a benzyl group, or together represent a heterocyclic ring having 3–7 members; and n represents an integer of 1–5;
wherein when A is $R^1$, B is $-(CH_2)_n-NR^2R^3$ and when A is $-(CH_2)_n-NR^2R^3$, B is $R^1$; and
wherein $R^4$ is selected from the group consisting of a hydrogen atom, a halogen atom, a lower alkyl group, a lower acyl group, a nitro group, a cyano group, an amino group, a lower alkoxycarbonyl group, a lower alkylamino group, a lower alkoxy group, a lower acyloxy group, a carbamoyl group, a lower alkylcarbamoyl group, and a lower acylamino group.

A hair growth promoting composition in accordance with the present invention is characterized by comprising said quinazolinone derivative or the pharmacologically acceptable salt thereof as an effective ingredient.

An external preparation for skin in accordance with the present invention is characterized by comprising said quinazolinone derivative or the pharmacologically acceptable salt thereof.

A method for promoting hair growth in accordance with the present invention is characterized by applying an effective amount of said quinazolinone derivative or the pharmacologically acceptable salt thereof on the skin of mammals and, in particular, on human skin.

BEST MODE FOR CARRYING OUT THE INVENTION

Figure 1:
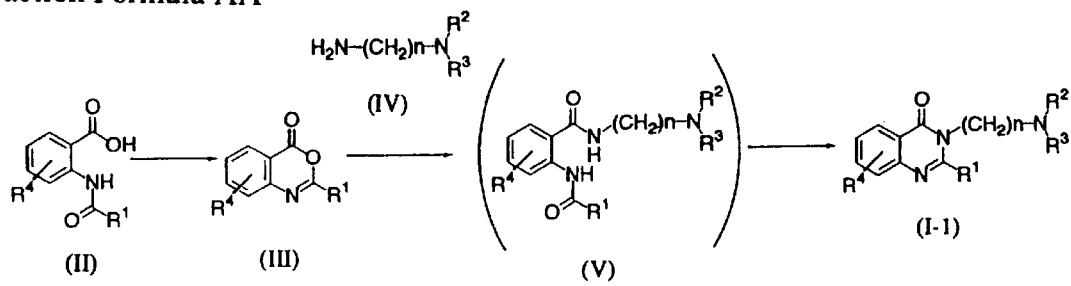
FIGS. 1–4 and FIGS. 7–10 show examples of steps for manufacturing the quinazolinone derivative in accordance with the present invention and FIGS. 5–6 and FIGS. 11–13 show examples of steps for manufacturing starting materials of the quinazolinone derivative in accordance with the present invention.

In a compound of the present invention, hydrocarbon group of $C_{10-30}$ shown by $R^1$ refers to a straight or branched alkyl group having 10–30 carbon atoms, a straight or branched alkenyl group having 10–30 carbon atoms or a straight or branched alkynyl group having 10–30 carbon atoms and may have a saturated ring or aromatic ring in $R^1$.

Examples of the above-mentioned straight alkyl group include decyl undecyl, dodecyl, tridecyl, tetradecyl, pentadecyl, hexadecyl, heptadecyl octadecyl, nonadecyl, icosyl, henicosyl, docosyl, tetracosyl, hexacosyl octacosyl and the like.

Examples of the above-mentioned branched alkyl group include 6-methyldecyl, 9-methyldecyl, 6-ethylnonyl, 5-propyloctyl, 11-methyldodecyl, 12-methyltridecyl, 4-methyltetradecyl, 13-methyltetradecyl, 14-ethylhexadecyl, 10-methyloctadecyl, 15-ethylheptadecyl, 10-methyldococyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of straight or branched alkenyl group having 10–30 carbon atoms and straight or branched alkynyl group having 10–30 carbon atoms include the alkenyl groups or alkynyl groups corresponding to the above-mentioned alkyl groups such as 4-decenyl, 7-dodecenyl, 9-octadodecenyl or 3-dodecenyl.

Also, examples of hydrocarbon group having a saturated ring or aromatic ring in $R^1$ include 12-cyclohexyldodecyl, 4-butylphenyl, 8-phenyloctyl, biphenylyl, and the like.

Among these groups, $R^1$ is preferably a straight or branched alkyl group having 10–30 carbon atoms and, more preferably, a straight or branched alkyl group having 10–25 carbon atoms and, particularly preferably, a straight alkyl group having 13–21 carbon atoms. The hair growth effect tends to deteriorate in the case where the carbon number of $R^1$ is too small.

Each of $R^2$ and $R^3$, which may be identical or different from each other, can be a hydrogen, a lower alkyl, a phenyl or a benzyl group. Also, $R^2$ and $R^3$ together can represent a heterocycle having 3–7 members.

In $R^2$ and $R^3$, the lower alkyl group refers to a straight or branched alkyl group having 1–6 carbon atoms. Examples of the lower allyl group include methyl, ethyl, propyl, butyl, isopropyl, isobutyl, 1-methylpropyl, tert-butyl, pentyl, 1-ethylpropyl, isoamyl, hexyl and the like. Methyl or ethyl group is preferable. In the present invention, the definition of lower alkyl group is the same as mentioned above if there is no further description.

In $R^2$ and $R^3$, a phenyl and a benzyl group may be unsubstituted or substituted by halogen, a lower alkyl a lower acyl, nitro, cyano, a lower alkoxycarbonyl a lower alkylamino, a lower alkoxy or a lower acyloxy group, respectively. The definition of each substituent referred in here is explained as follows:

Halogen atom represents chlorine, bromine, iodine or fluorine.

The lower alkyl group is as above-mentioned and, preferably, is methyl or ethyl group.

The lower acyl group is straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two and same or different lower alkyl group. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

In $R^2$ and $R^3$, the heterocycle having 3–7 members which is formed by $R^2$ and $R^3$ together represents a saturated or unsaturated heterocycle having 3–7 members containing nitrogen atom to which $R^2$ and $R^3$ are bonded. In addition to the nitrogen atom, a hetero atom such as nitrogen atom or oxygen atom may be contained in the heterocycle. Examples of the heterocycle include aziridine, azetidine, pyrrolidine, piperidine, homopiperidine, piperazine, morpholine, pyrrole, pyrazole, and imidazole ring. Among these heterocycles, pyrrolidine, piperidine, piperazine or morpholine ring is preferable. The heterocycle may be substituted by one or two of the same or different substituent. Such a substituent can be selected from the group consisting of a lower alkyl, a lower alkoxy, a lower acyl and a nitro group. The lower alkyl group is preferably methyl or ethyl. The lower alkoxy group is preferably methoxy or ethoxy group. The lower acyl group is preferably acetyl, propionyl or butyryl group.

Among them, $R^2$ and $R^3$ are preferably lower alkyl groups or a heterocycle having 3–7 members.

As for $R^4$, the definitions for halogen, lower alkyl, lower acyl, lower alkoxycarbonyl, lower alkylamino, lower alkoxy and lower acyloxy group are identical to those in $R^2$ and $R^3$ as mentioned above.

The lower alkylcarbamoyl group in $R^4$ represents a carbamoyl group whose one or two hydrogen atoms are substituted by a lower alkyl group. A preferable example of the lower alkylcarbamoyl group is methylcarbamoyl or ethylcarbamoyl group.

The lower acylamino group in $R^4$ represents an amino group whose one or two hydrogen atoms are substituted by a lower acyl group. The lower acyl group is as mentioned above. A preferable example of the lower acylamino group is acetylamino, propionylamino or benzoylamino group.

Preferably, $R^4$ is a hydrogen atom.

In the present invention, n represents an integer of 1–5 and, preferably, 2 or 3.

In Formula (I), although either A or B can be a hydrocarbon group of $C_{10-30}$ as shown by $R^1$ and a group as shown by —$(CH_2)_n$-$NR^2R^3$, from the manufacturing standpoint it is preferably that A is a group shown by $R^1$ and B is a group shown by —$(CH_2)_n$-$NR^2R^3$.

In the compound of the present invention shown by Formula (I), asymmetric carbon may exist in any group of $R^1$, $R^2$, $R^3$ or $R^4$. In addition to the various optical isomers based on such asymmetric carbon, the present invention can comprise geometrical isomers, conformational isomers, the other isomers and the mixture thereof.

The compound (I) provided in the present invention can be manufactured by using well-known reactions. Though the representative synthetic examples will be shown in the following, the present invention should not be restricted thereto. Also, in the following manufacturing methods, $R^1$, $R^2$, $R^3$, $R^4$ and n are the same as shown in the definitions of Formula (I), unless otherwise indicated.

COMPOUND (I-1) (A=$R^1$, B=$=(CH_2)_n$-$NR^2R^3$)

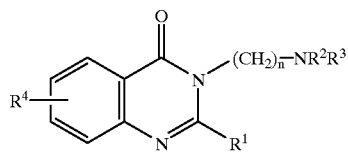

(I-1)

Compound (I-1) of the present invention can be synthesized as described in Reaction Formula AA in FIG. 1. Namely, an amidocarboxylic acid (II) is intramolecularly condensed to form Compound (III). Then, Compound (III) is reacted with amine (IV) to form Compound (V). Finally, Compound (V) is intramolecularly condensed, thereby producing Compound (I-1) of the present invention.

As in the first step of Reaction Formula AA, for example, a method proceeding by way of an acid halide or a mixed anhydride, which is a carboxyl group reactive derivative of Compound (II), can be used.

When the method proceeding by way of an acid halide is used, the amidocarboxylic acid (II) can be converted to its corresponding acid halide by using phosphorus pentachloride, phosphorus trichloride, or thionyl chloride. As an additive, an organic base such as triethylamine, pyridine or N-methylmorpholine can be used. As a solvent, for example, a halogenated hydrocarbon such as dichloromethane or chloroform; an aromatic compound such as benzene, toluene, xylene, or pyridine; an ether such as diethylether, tetrahydrofuran or 1,4-dioxane; an amide such as N,N-dimethylformamide or N,N-dimethylacetamide; or a mixed solvent thereof can be used. While the reaction temperature and reaction time may be changed according to the material compounds used, the reaction is usually effected at a temperature within the range of 0° C. to the reflux temperature of the solvent.

When the method proceeding by way of a mixed anhydride is used, the amidocarboxylic acid (II) can be converted to its corresponding mixed anhydride by using an activator such as ethyl chlorocarbonate, isobutyl chlorocarbonate, pivaloyl chloride, diphenylphosphinic chloride, or phosphorus oxychloride. As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as N,N-dimethylformamide or N,N-dimethylacetamide; or a sulfoxide such as dimethylsulfoxide can be used. While the reaction temperature and reaction time may be changed according to the material compounds used, the reaction is usually effected at a temperature within the range of –15° C. to the reflux temperature of the solvent.

The reaction of Compound (III) with amine (IV) at the second step in Reaction Formula AA can be effected with or without a solvent. Furthermore, as in the third step, Compound (V) can be intramolecularly condensed by continuous heating. As a solvent, for example, a halogenated hydrocarbon such as dichloromethane or chloroform; an aromatic compound such as benzene, toluene, xylene, or pyridine; an ether such as tetrahydrofuran or dioxane; an amide such as N,N-dimethylformamide or N,N-dimethylacetamide; or a sulfoxide such as dimethylsulfoxide can be used. The reaction temperature is usually within the range of room temperature to 150° C. Preferably, Compound (V) is produced without the solvent at a temperature within the range of room temperature to 100° C. and then intramolecularly condensed at 100° C.–150° C., thereby producing Compound (I-1) of the present invention.

Figure 2:
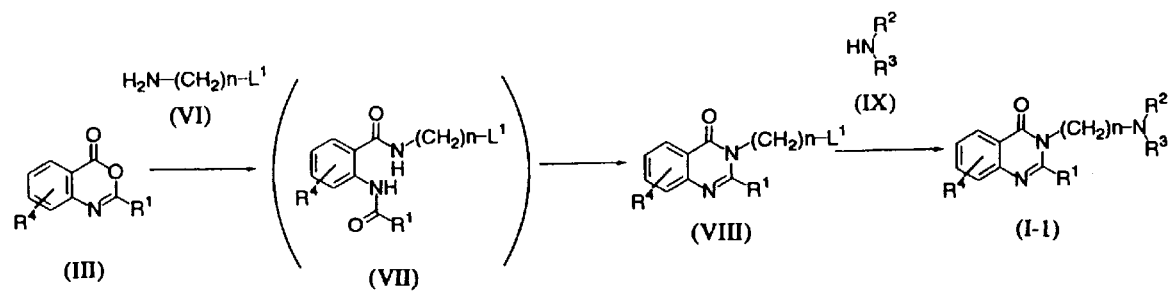

Also, Compound (I-1) of the present invention can be synthesized as shown in Reaction Formula AB of FIG. 2. First, Compound (III) is reacted with amine (VI) to form Compound (VII). Compound (VII) is then intramolecularly condensed to from Compound (VIII). Finally, Compound (VIII) is reacted with amine (IX) to produce Compound (I-1). Here, $L^1$ represents an atom or a group which is substituted by nitrogen easily and can be halogen, tosyloxy, mesyloxy group, or the like. The definition of $L^1$ throughout the rest of this specification is the same as shown above.

The first and second steps of Reaction Formula AB can be effected according to the reaction of the second and third steps in Reaction Formula AA, respectively.

The reaction at the third step in Reaction Formula AB can be effected in the presence of a base. As a base, for example, an inorganic base such as potassium carbonate, potassium hydroxide, sodium hydroxide or sodium hydride; or an organic base such as triethylamine or pyridine can be used. As a solvent, for example, toluene, ether, tetrahydrofuran, acetone or N,N-dimethylformamide can be used. Specifically, for example, by using potassium carbonate as a base, the reaction is effected in the solvent such as acetone or N,N-dimethylformamide at the temperature with the range of room temperature to the reflux temperature of the solvent, thereby attaining the aimed object.

Figure 3:
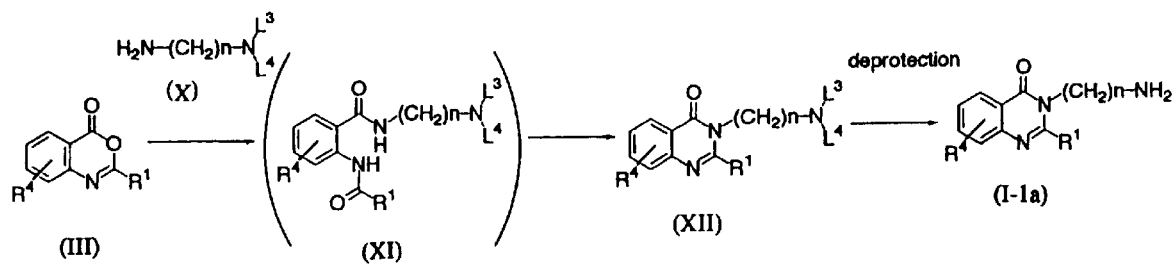

Also, Compound (I-1a) wherein $R^2$ and $R^3$ in Compound (I-1) are hydrogen atoms can be synthesized as shown in Reaction Formula AC of FIG. 3. First, Compound (III) is reacted with amine (X) to produce Compound (XI). Compound (XI) is then intramolecularly condensed to form Compound (XII). Finally, Compound (XII) is deprotected to produce Compound (I-1a). In Reaction Formula AC, at least one of $L^3$ and $L^4$ represents an amino protecting group which can be any protecting group unless it is adverse to the object of this Reaction Formula For example, either $L^3$ or $L^4$ can be an amino protecting group such as an urethane type protecting group (e.g., tert-butyloxycarbonyl, benzyloxycarbonyl or 9-fluorenylmethyloxycarbonyl group), a sulfonyl type protecting group (e.g., 2-(trimethylsilyl)ethanesulfonyl group), a sulfenyl type protecting group (e.g., 2,2,2-trifluoro-1,1-diphenylethanesulfenyl group), or an alkyl type protecting group (e.g., benzyl trityl or 9-phenylfluorenyl group), while the other can be a hydrogen atom. Also, $L^3$ and $L^4$ together can form a phthalimide type amino protecting group. The definition of $L^3$ and $L^4$ throughout the rest of this specification is the same as stated above.

The first and second steps in Reaction Formula AC can be effected according to the reactions of the second and third steps in Reaction Formula AA, respectively.

For the deprotection at the third step in Reaction Formula AC, various kind of known methods can be used according to the type of amino protecting group $L^3$ and $L^4$. Specifically, for example, in the case where $L^3$ is tert-butoxycarbonyl group and $L^4$ is hydrogen atom, the reaction is effected in a solvent such as glacial acetic acid by using hydrogen fluoride at the temperature within the range of room temperature to the reflux temperature of the solvent, thereby attaining the aimed object. Also, in the case where $L^3$ and $L^4$ together form a phthalimide type amino protecting group, by using hydrazine as a deprotection agent, the reaction is effected in ethanol at the temperature within the range of room temperature to the reflux temperature of the solvent, thereby attaining the aimed object.

Figure 4:
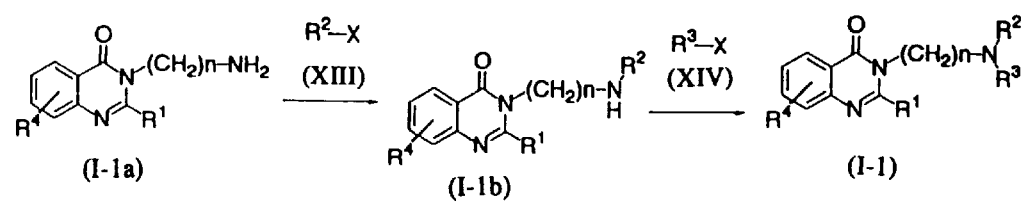

This Compound (I-1a), as shown in Reaction Formula AD of FIG. 4, can be converted into Compound (I-1b) of the present invention by reacting with about one equivalent amount of halogenated compound (XIII) in the presence of a base. Further, Compound (I-1) of the present invention can be obtained by reacting Compound (I-1b) with halogenated compound (XIV) in the similar manner to the above. X represents halogen atom. The definition of X throughout the rest of this specification remains the same.

In this reaction, when $R^2$ and $R^3$ are lower alkyl phenyl or benzyl groups, as a base, an inorganic base such as potassium carbonate, potassium hydroxide, sodium hydroxide or sodium hydride; or an organic base such as triethylamine or pyridine can be used. Specifically, for example, by using potassium carbonate as the base, the reaction is effected in the solvent such as acetone or N,N-dimethylformamide at the temperature within the range of room temperature to the reflux temperature of the solvent, thereby attaining the aimed object.

In the similar manner to this Reaction Formula AD, by reacting Compound (I-1a) of the present invention with about twice equivalent amount of halogenated compound (XIIII) in the presence of the base, the compound of the present invention wherein $R^2$ and $R^3$ in formula (I-1) are the same can be obtained. Also, by reacting Compound (I-1a) with a suitable dihalogenated compound, the compound of the present invention wherein $R^2$ and $R^3$ in formula (I-1) together form a heterocycle having 3–7 members can be obtained.

Figure 5:
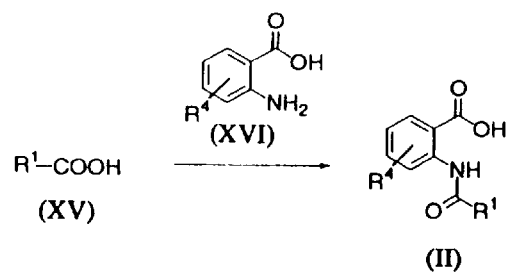

The amidocarboxylic acid (II), which is a starting material in Reaction Formula AA, as shown in Reaction Formula AE of FIG. 5, can be synthesized by converting carboxylic acid (XV) to acid halide or mixed anhydride according to the method at the first step in Reaction Formula AA, and then reacting the latter with Compound (XVI).

Figure 6:
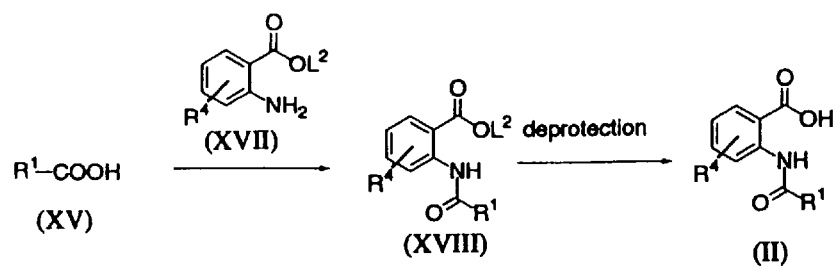

Also, as shown in Reaction Formula AF of FIG. 6, the amidocarboxylic acid (II) can be synthesized by deprotecting amide (XVIII) which is synthesized according to known amide-forming reaction from amine (XVII) with a suitable carboxylic acid (XV). $L^2$ represents a carboxyl protecting group and can be a lower alkyl group such as methyl, ethyl or tert-butyl group; phenacyl group; trichloroethyl group or the like as long as it is not adverse to the successive reactions. The definition of $L^2$ throughout the rest of this specification remains the same.

As for the amide-forming reaction at the first step in Reaction Formula AF, any known method such as the mixed anhydride method, the acid chloride method, the DCC method, the CDI method and the azide method can be used unless any problem occur in particular.

The mixed anhydride method and the acid chloride method can be effected according to the reaction at the first step in Reaction Formula AA.

In the DCC method, as a condensing agent, N,N-dicyclohexylcarbodiimide (DCC), 1-ethyl-3-(3-dimethylaminopropyl)carbodiimide hydrochloride (WSCI) and the like can be used. As a solvent, for example, a halogenated hydrocarbon such as dichloromethane or chloroform; an aromatic compound such as benzene, toluene, or xylene; an ether such as tetrahydrofuran or 1,4-dioxane; or an amide such as N,N-dimethylformamide or N,N-dimethylacetamide can be used. If necessary, this reaction may be effected while 1-hydroxy benzotriazole (HOBt) or N-hydroxysuccinimide (HOSu) is added thereto. While the reaction temperature and reaction time may be changed according to the material compounds used, the reaction is usually effected at a temperature within the range of 0° C. to the reflux temperature of the solvent.

In the CDI method, an activator such as N,N-carbonyldiimidazole is used to convert the carboxylic acid (XV) into the corresponding N-acyl derivative and then the latter is reacted with the amine (XVII). As an additive, for example, an organic base such as triethylamine, pyridine, or N-methylmorpholine; or an inorganic base such as sodium hydride or potassium hydride can be used. As a solvent, for example, a halogenated hydrocarbon such as dichloromethane or chloroform; an aromatic compound such as benzene, toluene or xylene; an ether such as tetrahydrofuran or 1,4-dioxane; an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

In the azide method, an activator such as diphenylphosphorylazide is used to convert the carboxylic acid (XV) into its corresponding azide and then the latter is reacted with the amine (XVII). As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene or xylene; an ether such as tetrahydrofuran or 1,4-dioxane; an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

The deprotection at the second step in Reaction Formula AF can be effected by hydrolysis in the presence of an acid or a base. Hydrochloric acid, sulfuric acid, p-toluenesulfonic acid or the like can be used as the acid, while sodium hydroxide, potassium hydroxide, potassium tert-butoxide, or the like can be used as a base. As a solvent, an alcohol such as methanol or ethanol, water, a mixed solvent thereof, or the like can be used. While the reaction temperature and reaction time can be changed according to the material compounds used, the reaction is usually effected at a temperature within the range of 0° C. to the reflux temperature of the solvent.

COMPOUND (I-2) (A=—$(CH_2)_n$-$NR^2R^3$), B=$R^1$)

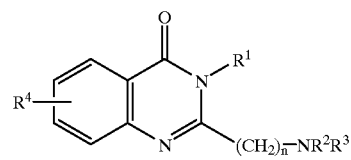

(I-2)

Figure 7:
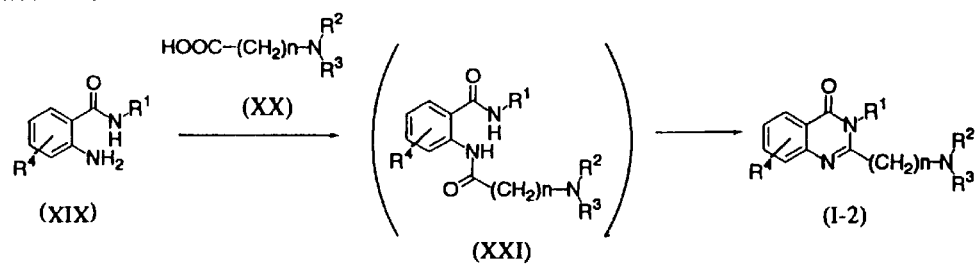

Compound (1–2) of the present invention, as shown in Reaction Formula BA of FIG. 7, can be synthesized by way of Compound (XXI) from amine (XIX) and carboxylic acid (XX). As for the first step of Reaction Formula BA, known amide-forming reactions as shown at the first step in Reaction Formula AF can be used. Also, the reaction at the second step can be effected according to the intramolecular condensation reaction at the third step in Reaction Formula AA.

Figure 8:
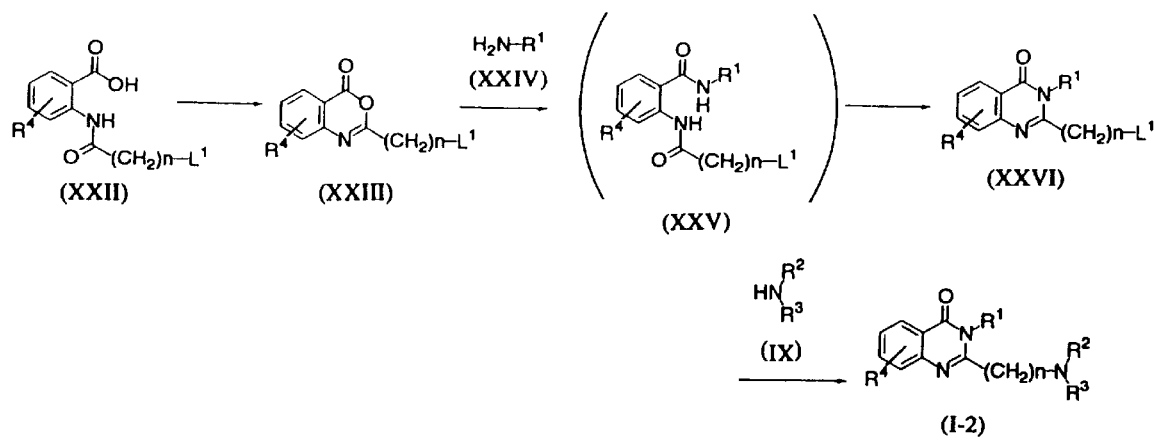

Also, Compound (I-2) of the present invention can be synthesized as shown in Reaction Formula BB of FIG. 8. In Reaction Formula BB, an amidocarboxylic acid (XXII) is converted into its intramolecularly condensed compound (XXIII) and then the latter is reacted with amine (XXIV) to form Compound (XXV). Compound (XXV) is then intramolecularly condensed to form Compound (XXVI). Finally, Compound (XXVI) is reacted with amine (IX), thereby producing Compound (I-2) of the present invention.

The reactions at the first to the third steps in Reaction Formula BB can be effected according to Reaction Formula AA.

The reaction at the fourth step in Reaction Formula BB can be effected according to the reaction at the third step in Reaction Formula AB.

Figure 9:
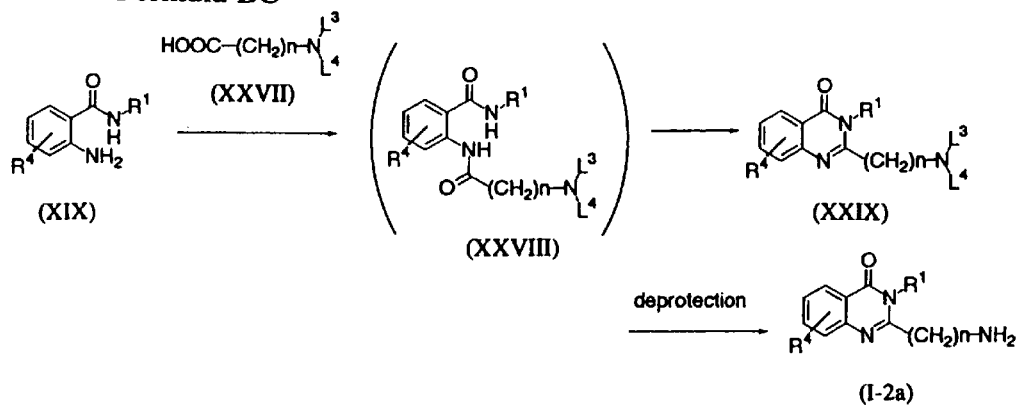

Also, Compound (I-2a) where $R^2$ and $R^3$ are hydrogen atom in Compound (I-2) of the present invention, as shown in Reaction Formula BC of FIG. 9, can be synthesized by deprotecting Compound (XXIX) which is synthesized by way of Compound (XXVIII) from amine (XIX) with carboxylic acid (XXVII).

The first step in Reaction Formula BC can be effected according to known amide-forming reaction as the first step of Reaction Formula AF.

The second step of Reaction Formula BC can be effected according to the reaction of the third step in Reaction Formula AA.

The deprotection at the third step in Reaction Formula BC can be effected according to the reaction at the third step in Reaction Formula AC.

Figure 10:
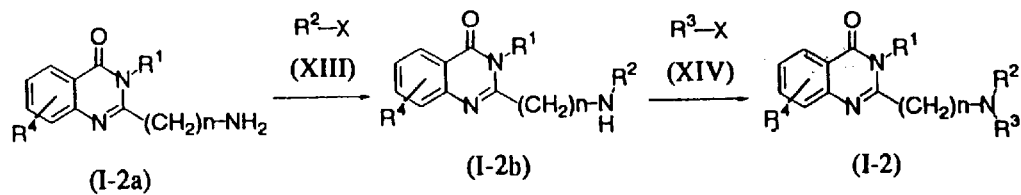

This Compound (I-2a), as shown in Reaction Formula BD of FIG. 10, can be converted into Compound (I-2b) of the present invention by reacting with about one equivalent amount of halogenated compound (XIII) in the presence of a base. Further, by reacting Compound (I-2b) with halogenated compound (XIV) in the similar manner to the above, Compound (I-2) can be obtained. This reaction can be effected according to Reaction Formula AD.

In the similar manner to this Reaction Formula BD, by reacting Compound (I-2a) of the present invention with about twice equivalent amount of halogenated compound (XIII) in the presence of the base, the compound of the present invention wherein $R^2$ and $R^3$ in formula (I-2) are the same can be obtained Also, by reacting Compound (I-2a) with a suitable dihalogenated compound, the compound of the present invention wherein $R^2$ and $R^3$ in formula (I-2) together form a heterocycle having 3–7 members can be obtained.

Figure 11:
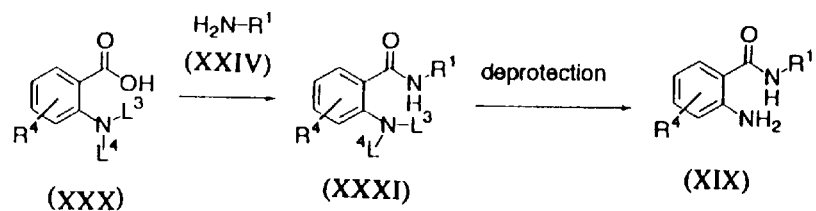

The amine (XIX) which is a starting material in Reaction Formulas BA and BC, as shown in Reaction Formula BE of FIG. 11, can be obtained by synthesizing amide from carboxylic acid (XXX) and amine (XXIV) and subjecting thus obtained amide (XXXI) to deprotection. The first step in this reaction can be effected according to the method at the first step in Reaction Formula AF. The deprotection reaction at the second step can be effected according to the method at the third step in Reaction Formula AC.

Figure 12:
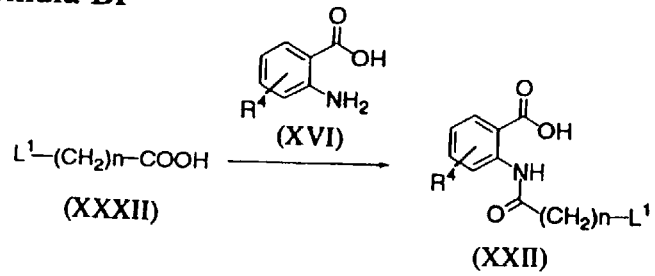

The carboxylic acid (XXII), which is a starting material in Reaction Formula BB, as shown in Reaction Formula BF of FIG. 12, can be synthesized from carboxylic acid (XXXII) and Compound (XVI). This reaction can be effected according to the method in Reaction Formula AE.

Figure 13:
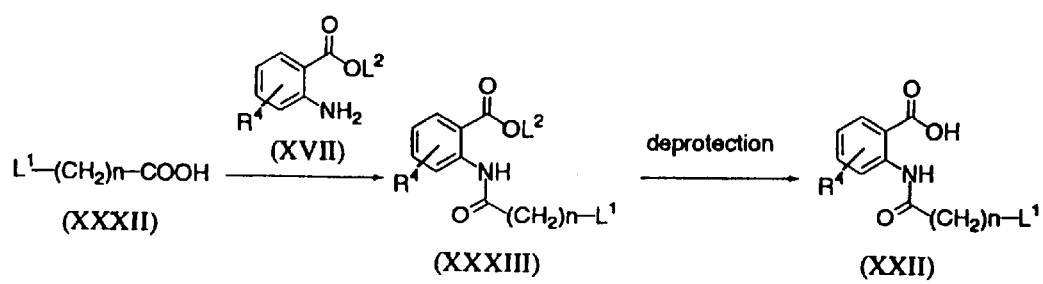

Also, as shown in Reaction Formula BG of FIG. 13, the carboxylic acid (XXII) can be synthesized by deprotecting Compound (XXXIII) which is synthesized from carboxylic acid (XXXII) with Compound (XVII). This reaction can be effected according to the method in Reaction Formula AF.

Among the starting materials used in the foregoing Reaction Formulas, materials which are not described above are commercially available or can be easily synthesized from a suitable material compound by using known methods.

The quinazolinone derivative provided in the present invention can be changed to an acid-added salt if necessary. Examples of the acid-added salt include salt with inorganic acid such as hydrochloric acid, hydrobromic acid, sulfuric acid or phosphoric acid and salts with organic acid such as acetic acid, propionic acid, citric acid, lactic acid, oxalic acid, maleic acid, fumaric acid, succinic acid, tartaric acid or methansulfonic acid. These salts can be easily manufactured by common methods.

The quinazolinone derivatives in accordance with the present invention, which mechanism of action has not been made clear, have an excellent hair growth and regrowth promoting effect. Accordingly, by applying the compound on skin of mammals and, in particular, on human scalp, care, improvement, or prevention of hair loss can be expected.

The quinazolinone derivative of the present invention can apply to pathological alopecia such as alopecia areata, alopecia pityrodes or alopecia seborrheica in addition to thin hair or hair loss what is called male pattern baldness or androgenic alopecia. The dosage of the quinazolinone derivative in accordance with the present invention must be determined suitably according to sex, age and degree of symptom in hair loss or thin hair. Usually 0.01–20 mg/cm$^2$ is applied on scalp per day for an adult in a single dose or several doses.

When the quinazolinone derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical forms include tonic, lotion, milky lotion, cream, ointment, gel, spray and mousse.

In addition to the quinazolinone derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin B$_6$.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, rosmarinus officinalis, drynaria, cytisus scoparius, gentiana, salviae miltiorrhizeae radix, sponge gourd, platycodon, pinus, sophora root, Japanese angelica root, safflower, Japanese barberry, areca, eucalyptus, prunella spike, akebia stem, achyranthes root, bupleurum root, tea, licorice, hop, Chrysanthemum, senega, sesame, cnidium rhizome, cashew, pueraria root, rosae rugosae flos, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives;

lactic acid and its alkyl ester; an organic acid such as citric acid; a protease inhibitor such as tranexamic acid; and the like can be compounded.

Further, an alcohol such as ethanol or isopropyl alcohol; a polyvalent alcohol such as glycerine, propylene glycol or polyethylene glycol; an oily ingredient such as higher fatty acids, higher alcohols, hydrogenated castor oils, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

HAIR REGROWTH TEST (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the test compound was applied on the shaved portion once a day. For hair regrowth effect of the test compound, the hair regrowth area of mice's region of back was measured and ratio of the hair regrowth area with respect to the shaved area was evaluated as hair regrowth area rate.

(2) Result

Hair regrowth area rates (%) after the following tested compounds were applied for 18 days are shown in TABLE 1:

Compound 1: 3-{3-(Dimethylamino)propyl}-2-heptadecy-3-hydroquinazolin-4-one

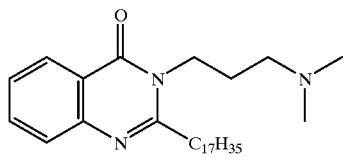

Compound 2: 3-{3-(Dimethylamino) propyl}-2-heptadecyl-3-hydroquinazolin-4-one monohydrochloride

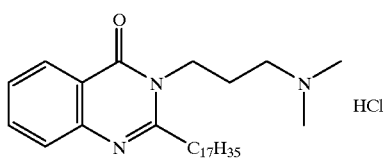

Compound 3: 3-{3-(Dimethylamino)propyl}-2-heptadecyl-3-hydroquinazolin-4-one dihydrochloride

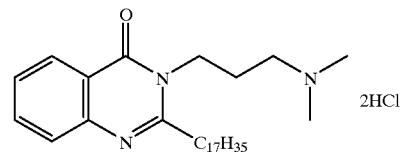

Compound 4: 3-{3-(Dimethylamino)propyl}-2-tridecyl-3-hydroquinazolinone-4-one

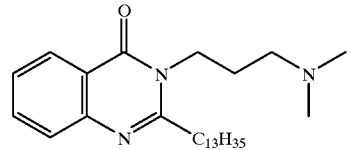

Compound 7: 3-{3-(Dimethylamino)propyl}-2-henicosyl-3-hydroquinazolin-4-one monohydrochloride

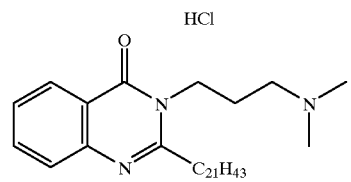

TABLE 1

| Compound | Concentration of Compound (w/v %) | Hair Regrowth Area Rate (%) |
| --- | --- | --- |
| Ethanol (negative contrast) | — | 0 |
| Compound 1 | 0.1 | 100 |
| Compound 2 | 0.1 | 100 |
| Compound 3 | 0.1 | 55 |
| Compound 4 | 0.1 | 66 |
| Compound 7 | 0.2 | 83 |

As is clear from the TABLE 1, quinazolinone derivatives and their pharmacologically acceptable salts in accordance with the present invention show excellent hair regrowth and growth promoting effects.

In the following, examples of compounds and compositions in accordance with the present invention will be explained. However the present invention should not be restricted thereto.

EXAMPLE 1-1

3-{3-(Dimethylamino)propyl}-2-heptadecyl-3-hydroquinazolin-4-one (Compound 1)

(1) Ethyl 2-(octadecanoylamino)benzoate

Triethylamine (1.86 ml) and octadecanoyl chloride (3.67 g) were added to a solution of ethyl anthranilate (2.00 g) in methylene chloride (20 ml). After being stirred for 30 minutes at room temperature, the reaction mixture was diluted with chloroform, washed with saturated sodium hydrogencarbonate aqueous solution and water successively, dried over sodium sulfate anhydride, and concentrated, thereby yielding 5.45 g of the aimed compound as colorless crystals.

$^1$H-NMR (CDCl$_3$) δ: 0.88 (3H, t, J=7.3 Hz), 1.2–1.45 (28H, m), 1.42 (3H, t, J=7.3 Hz), 1.75 (2H, quintet, J=37.3 Hz), 2.43 (2H, t, J=7.3 Hz), 4.38 (2H, q, J=7.3 Hz), 7.06 (1H, m), 7.53 (1H, m), 8.04 (1H, dd, J=7.8, 1.5 Hz), 8.74 (1H, d, J=8.3 Hz), 11.10 (1H, brs).

(2) 2-(Octadecanoylamino)benzoic acid

A sodium hydroxide solution (NaOH 0.14 g / water 2 ml) was added to a solution of ethyl 2-(octadecanoylamino) benzoate (1.00 g) in ethanol (10 ml). After being stirred for 4 hours at room temperature, the reaction mixture was concentrated. The residue, with ethyl acetate added thereto, was washed with diluted hydrochloric acid, water and saturated brine successively, dried over sodium sulfate anhydride, and concentrated. The residue was recrystallized from hexane-ethyl acetate mixed solution, thereby yielding 0.85 g of the aimed compound as colorless crystals.

$^1$H-NMR (CDCl$_3$) δ: 0.88 (3H, t, J=6.8 Hz), 1.2–1.45 (28H, m), 1.76 (2H, quintet, J=7.3 Hz), 2.48 (2H, t, J=7.3 Hz), 7.12 (1H, m), 7.60 (1H, m), 8.12 (1H, m), 8.77 (1H, d, J=8.3 Hz), 10.90 (1H, brs).

(3) 3-{3-(Dimethylamino)propyl}-2-heptadecyl-3-hydroquinazolin-4-one

Triethylamine (0.44 ml) and diphenylphosphinic chloride (0.48 ml) were added to a suspension of 2-(octadecanoylamino)benzoic acid (0.85 g) in methylene chloride (10 ml). After being stirred for 3 hours at 0° C., the mixture, with N,N-dimethyl-1,3-propanediamine (0.33 ml) added thereto, was stirred for 44 hours at room temperature. The reaction mixture was then diluted with chloroform, washed with saturated sodium hydrogencarbonate aqueous solution and water successively, dried over sodium sulfate anhydride, and concentrated. The residue was purified by silica gel column chromatography (silica gel 20 g, chloroform-methanol), thereby yielding 0.53 g of N-{2-{N-{3-(dimethylamino)propyl}carbamoyl}phenyl}octadecaneamide and 0.37 g of the aimed compound as colorless crystals.

N-{2-{N-{3-(Dimethylamino)propyl}carbamoyl}-phenyl}octadecaneamide $^1$H-NMR (CDCl$_3$) δ: 0.88 (3H, t, J=6.8 Hz), 1.2–1.45 (28H, m), 1.7–1.85 (4H, m), 2.30 (6H, s), 2.40 (2H, t, J=7.6 Hz), 2.52 (2H, t, J=5.6 Hz), 3.52 (2H, m), 7.01 (1H, m), 7.39–7.44 (2H, m), 8.64 (1H, d, J=8.3 Hz), 8.91 (1H, brs), 11.58 (1H, brs).

3-{3-(Dimethylamino)propyl}-2-heptadecyl-3-hydroquinazolin-4-one $^1$H-NMR (CDCl$_3$) δ: 0.88 (3H, t, J=6.6 Hz), 1.2–1.4 (26H, m), 1.46 (2H, m), 1.84 (2H, m), 1.90 (2H, m), 2.26 (6H, s), 2.40 (2H, t, J=6.8 Hz), 2.85 (2H, t, J=7.8 Hz), 4.15 (2H, t, J=7.8 Hz), 7.70 (1H, m), 8.24 (1H, d, J=8.3 Hz).

EXAMPLE 1-2

3-{3-(Dimethylamino)propyl}-2-heptadecyl-3-hydroquinazolin-4-one (Compound 1)

(1) 2-(Octadecanoylamino)benzoic acid

Triethylamine (0.46 ml) was added to a suspension of stearic acid (853 mg) in methylene chloride (8.5 ml). Then, ethyl chlorocarbonate (0.32 ml) was dropwise added to the mixture while being cooled with ice. After being stirred for 1 hour at 0° C., the mixture, with a solution of anthranilic acid (411 mg) and triethylamine (0.42 ml) in methylene chloride (2 ml) dropwise added thereto, was stirred for 16 hours at 45° C. The reaction mixture was then diluted with chloroform, washed with water and saturated brine successively, dried over sodium sulfate anhydride, and concentrated. The residue was recrystallized from hexane-ethyl acetate mixed solution, thereby yielding 1.107 g of the aimed compound as colorless crystals. According to the comparison by using TLC and $^1$H-NMR, this product was identified as the aimed compound obtained by Example 1-1 (2).

(2) 3-{3-(Dimethylamino)propyl}-2-heptadecyl-3-hydroquinazolin-4-one

Triethylamine (0.14 ml) was added to a suspension of 2-(octadecanoylamino)benzoic acid (404 mg) in methylene chloride (5 ml). Then, diphenylphosphinic chloride (0.19 ml) was added to the mixture while being cooled with ice. After being stirred for 3 hours at 0° C., the reaction mixture, with N-N-dimethyl-1,3-propanediamine (0.14 ml) added thereto, was stirred for 13 hours at room temperature and for 24 hours at 50° C. successively. The reaction mixture was then diluted with ethyl acetate, washed with water, saturated sodium hydrogencarbonate aqueous solution and saturated brine successively, dried over magnesium sulfate anhydride, and concentrated. The residue was purified by silica gel column chromatography (silica gel 35 g, chloroform-methanol), thereby yielding 87 mg of N-{2-{N-{3-(dimethylamino)propyl}carbamoyl}phenyl}octadecaneamide and 203 mg of the aimed compound as colorless crystals. According to the comparison by using TLC and $^1$H-NMR, these products were identified as N-{2-{N-{3-(dimethylamino)propyl}carbamoyl}phenyl}octadecaneamide and the aimed compound obtained by Example 1-1 (3), respectively.

EXAMPLE 1-3

3-{3-(Dimethylamino)propyl}-2-heptadecyl-3-hydroquinazolin-4-one (Compound 1)

Toluene (5 ml) was added to N-{2-(N-{3-(dimethylamino)propyl}carbamoyl}phenyl}octadecaneamide (211 mg) obtained by Example 1-1 (3) or Example 1-2 (2). After being refluxed with stirring for 23 hours at 130° C., the reaction mixture was purified by silica gel column chromatography (silica gel 25 g, chloroform-methanol), thereby yielding 116 mg of the aimed compound as colorless crystals. According to the comparison by using TLC and $^1$H-NMR, this product was identified as the aimed compound obtained by Example 1-1 (3). The starting material (39 mg) was recovered at the same time.

EXAMPLE 1-4

3-{3-(Dimethylamino)propyl}-2-heptadecyl-3-hydroquinazolin-4-one (Compound 1)

(1) 2-Heptadecyl-4H-3,1-benzoxazin-4-one

Triethylamine (0.46 ml) was added to a suspension of stearic acid (853 mg) in methylene chloride (8.5 ml). Then, ethyl chlorocarbonate (0.32 ml) was dropwise added to the mixture while being cooled with ice. After being stirred for 1 hour at 0° C., the mixture, with a mixed solution of anthranilic acid (411 mg) and triethylamine (0.42 ml) in methylene chloride (2 ml) dropwise added thereto, was stirred for 16 hours at 45C and cooled with ice. The reaction mixture, with triethylamine (0.46 ml) and ethyl chlorocarbonate (0.32 ml) dropwise added thereto, was stirred for 1 hour at 0° C. and for 1.5 hours at room temperature successively, and then concentrated. The residue, with ethyl acetate added thereto, was washed with water, neutralized with diluted hydrochloric acid, and washed with saturated brine. The organic layer was dried over magnesium sulfate anhydride and then concentrated. The residue was purified by silica gel column chromatography (silica gel 35 g, chloroform-methanol), thereby yielding 966 mg of the aimed compound as colorless crystals.

$^1$H-NMR (CDCl$_3$) δ: 0.88 (3H, t, J=6.8 Hz), 1.2–1.45 (28H, m), 1.83 (2H, quintet, J=7.8 Hz), 2.68 (2H, t, J=7.8 Hz), 7.50 (1H, ddd, J=7.8, 7.3, 1.0 Hz), 7.56 (1H, d, J=8.3 Hz), 7.79 (1H, ddd, J=8.3, 7.3, 1.5 Hz), 8.19 (1H, dd, J=7.8, 1.5 Hz).

(2) 3-{3-(Dimethylamino)propyl}-2-heptadecyl-3-hydroquinazolin-4-one

N,N-Dimethyl-1,3-propanediamine (0.14 ml) was added to 2-heptadecyl-4H-3,1-benzoxazin-4-one (385 mg). The mixture was stirred for 2 hours at 70° C. and for 3 hours at 130° C. successively. The reaction mixture was purified by silica gel column chromatography (silica gel 25 g, chloroform-methanol), thereby yielding 368 mg of the aimed compound as colorless crystals. According to the comparison by using TLC and $^1$H-NMR, this product was identified as the aimed compound obtained by Example 1-1 (3).

EXAMPLE 2

3-{3-(Dimethylamino)propyl}-2-heptadecyl-3-hydroquinazolin-4-one monohydrochloride (Compound 2)

4N Hydrochloric acid-ethyl acetate solution (0.19 ml) was dropwise added to a solution of 3-{3-(dimethylamino)propyl}-2-heptadecyl-3-hydroquinazolin-4-one (335 mg) in ethyl acetate (3 ml) while being cooled with ice. After the mixture was stirred for 30 minutes at 0° C., the deposited crystals were collected by filtration under a vacuum, washed with ethyl acetate, and dried, thereby yielding 336 mg of the aimed compound as colorless crystals.

$^1$H-NMR (CDCl$_3$) δ: 0.88 (3H, t, J=6.8 Hz), 1.2–1.4 (26H, m), 1.48 (2H, m), 1.85 (2H, quintet, J=7.8 Hz), 2.38 (2H, m), 2.82 (6H, s), 2.84 (2H, t, J=7.8 Hz), 3.17 (2H, t, J=8.1 Hz), 4.25 (2H, t, J=6.8 Hz), 7.45 (1H, m), 7.66 (1H, d, J=7.8 Hz), 7.74 (1H, m), 8.19 (1H, dd, J=8.3, 1.5 Hz), 12.75 (1H, brs).

EXAMPLE 3

3-{3-(Dimethylamino)propyl}-2-heptadecyl-3-hydroquinazolin-4-one dihydrochloride (Compound 3)

4N hydrochloric acid-ethyl acetate solution (0.32 ml) was dropwise added to a solution of 3-{3-(dimethylamino)propyl}-2-heptadecyl-3-hydroquinazolin-4-one (282 mg) in ethyl acetate (3 ml) while being cooled with ice, and then the mixture was stirred for 30 minutes at 0° C. The deposited crystals were collected by filtration under a vacuum washed with ethyl acetate, and dried, thereby yielding 306 mg of the aimed compound as colorless crystals.

$^1$H-NMR (CDCl$_3$) δ: 0.88 (3H, t, J=6.7 Hz), 1.2–1.4 (26H, m), 1.50 (2H, m), 1.85 (2H, m), 2.56 (2H, m), 2.87 (3H, s), 2.89 (3H, s), 3.28 (4H, m), 4.39 (2H, t, J=6.7 Hz), 7.59 (1H, m), 7.3 (1H, m), 8.10 (1H, brd), 8.24 (1H, d, J=8.2 Hz).

EXAMPLE 4

3-{3-(Dimethylamino)propyl}-2-tridecyl-3-hydroquinazolin-4-one (Compound 4)

(1) 2-Tridecyl-4H-3,1-benzoxazin-4-one

Triethylamine (1.76 ml) was added to a suspension of anthranilic acid (823 mg) in methylene chloride (20 ml). Then, myristoyl chloride (1.63 ml) was dropwise added to the mixture while being cooled with ice. After being stirred for 2.5 hour at room temperature, the reaction mixture was cooled with ice. Triethylamine (0.92 ml) and ethyl chlorocarbonate (0.63 ml) were dropwise added to the reaction mixture successively. After being stirred for 1 hour at 0° C. and for 1.5 hours at room temperature successively, the reaction mixture was concentrated. The residue, with ethyl acetate added thereto, was washed with water, neutralized with diluted hydrochloric acid, and washed with saturated brine. The organic layer was dried over magnesium sulfate anhydride and then concentrated. The residue was purified by silica gel column chromatography (silica gel 60 g, chloroform-hexane), thereby yielding 1.663 g of the aimed compound as colorless crystals.

$^1$H-NMR (CDCl$_3$) δ: 0.88 (3H, t, J=6.8 Hz), 1.2–1.45 (20H, m), 1.83 (2H, quintet, J=7.8 Hz), 2.68 (2H, t, J=7.8 Hz), 7.50 (1H, m), 7.56 (1H, d, J=8.3 Hz), 7.79 (1H, m), 8.19 (1H, dd, J=8.3, 1.5 Hz).

(2) 3-{3-(Dimethylamino)propyl}-2-tridecyl-3-hydroquinazolin-4-one

N,N-Dimethyl-1,3-propanediamine (0.34 ml) was added to 2-tridecyl-4H-3,1-benzoxazin-4-one (817 mg). Then, the mixture was stirred for 2 hours at 70° C. and for 21 hours at 140° C. successively. The reaction mixture was purified by silica gel column chromatography (silica gel 35 g, chloroform-methanol), thereby yielding 746 mg of the aimed compound as colorless solid.

$^1$H-NMR (CDCl$_3$) δ: 0.88 (3H, t, J=6.8 Hz), 1.2–1.4 (18H, m), 1.46 (2H, m), 1.84 (2H, m), 1.90 (2H, m), 2.25 (6H, s), 2.39 (2H, t, J=6.8 Hz), 2.85 (2H, t, J=8.1 Hz), 4.15 (2H t, J=7.8 Hz), 7.42 (1H, m), 7.62 (1H, d, J=8.3 Hz), 7.70 (1H, m), 8.24 (1H, dd, J=8.3, 1.5 Hz).

EXAMPLE 5

2-Heptadecyl-3-(3-morpholinopropyl)-3-hydroquinazolin-4-one (Compound 5)

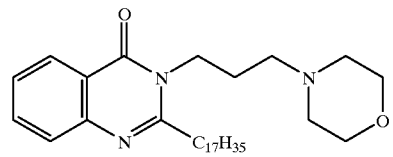

N-(3-Aminopropyl)morpholine (0.63 ml) was added to 1-heptadecyl-4H-3,1-benzoxazin-4-one (1.500 g). The mixture was stirred for 2 hours at 70° C. and then, further stirred for 21 hours at 130° C. The reaction mixture was purified by silica gel column chromatography (silica gel 50 g, chloroform-ethyl acetate), thereby yielding 1.137 g of the aimed compound as colorless solid.

$^1$H-NMR (CDCl$_3$) δ: 0.88 (3H, t, J=6.8 Hz), 1.2–1.4 (26H, m), 1.47 (2H, m), 1.83 (2H, m), 1.93 (2H, m), 2.45 (6H, m), 2.85 (2H, t, J=7.8 Hz), 3.69 (4H, m), 4.17 (2H t, J=7.6 Hz), 7.42 (1H, m), 7.62 (1H, dd, J=7.8, 1.0 Hz), 7.71 (1H, m), 8.23 (1H, dd, J=8.1, 1.0 Hz).

EXAMPLE 6

3-{3-(Dimethylamino)propyl}-2-henicosyl-3-hydroquinazolin-4-one (Compound 6)

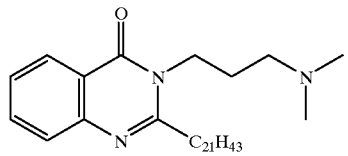

(1) 2-Henicosyl-4H-3,1-benzoxazine-4-one

Triethylamine (1.58 ml) was added to a suspension of behenic acid (3.51 g) in methylene chloride (35 ml). Then, ethyl chlorocarbonate (1.08 ml) was dropwise added to the mixture while being cooled with ice. After being stirred for 1.5 hours at 0° C., the mixture, with a mixed solution of anthranilic acid (1.42 g) and triethylamine (1.44 ml) in methylene chloride (7 ml) dropwise added thereto, was stirred for 3 hour at 0° C. and for 15 hours at room temperature successively, and then cooled with ice. The reaction mixture, with triethylamine (1.58 ml) and ethyl chlorocarbonate (1.08 ml) dropwise added thereto, was stirred for 1 hour at 0° C. and for 2.5 hours at room temperature successively, and then concentrated. The residue, with chloroform added thereto, was washed with water and saturated brine successively. The organic layer was dried over sodium sulfate anhydride, and then concentrated. The residue was purified by silica gel column chromatography (silica gel 100 g, hexane-chloroform), thereby yielding 3.39 g of the aimed compound as colorless solid.

$^1$H-NMR (CDCl$_3$) δ: 0.88 (3H, t, J=6.8 Hz), 1.1–1.4 (34H, m), 1.41 (2H, m), 1.83 (2H, quintet, J=7.8 Hz), 2.68 (2H, t, J=7.8 Hz), 7.50 (1H, ddd, J=7.8, 7.3, 1.0 Hz), 7.56 (1H, d, J=3 Hz), 7.79 (1H, ddd, J=8.3, 7.3, 1.5 Hz), 8.19 (1H, dd, J=7.8, 1.5 Hz).

(2) 3-{3-(Dimethylamino)propyl}-2-henicosyl-3-hydroquinazolin-4-one

N,N-Dimethyl-1,3-propanediamine (0.44 ml) was added to 2-henicosyl-4H-3,1-benzoxazine-4-one (1.38 g). Then, the mixture was stirred for 2.5 hours at 70° C. and for 20 hours at 130° C. successively. The reaction mixture, with ethyl acetate added thereto, was washed with saturated brine. The organic layer was dried over sodium sulfate anhydride, and then concentrated. The residue was purified by silica gel column chromatography (silica gel 50 g, chloroform-methanol), thereby yielding 1.23 g of the aimed compound as light-yellow solid.

$^1$H-NMR (CDCl$_3$) δ: 0.88 (3H, t, J=6.8 Hz), 1.1–1.4 (34H, m), 1.46 (2H, m), 1.84 (2H, quintet, J=7.8 Hz), 1.90 (2H, dd, J=7.8, 6.8 Hz), 2.25 (6H, s), 2.39 (2H, t, J=6.8 Hz), 2.86 (2H, t, J=37.8 Hz), 4.15 (2H, t, J=7.8 Hz), 7.42 (1H, m), 7.62 (1H, d, J=7.8 Hz), 7.70 (1H, m), 8.24 (1H, d, J=7.8 Hz).

EXAMPLE 7

3-{3-(Dimethylamino)propyl}-2-henicosyl-3-hydroquinazolin-4-one monohydrochloride (Compound 7)

4N hydrochloric acid-ethyl acetate solution (0.57 ml) was dropwise added to a solution of 3-{3-(dimethylamino)propyl}-2-henicosyl-3-hydroquinazolin-4-one (1.10 g) in ethyl acetate (11 ml) while being cooled with ice. After being stirred for 20 minutes at 0° C., the mixture was concentrated. The residue was recrystallized from ethanol-ethyl acetate, thereby yielding 1.03 g of the aimed compound as colorless crystals.

$^1$H-NMR (CDCl$_3$) δ: 0.88 (3H, t, J=6.8 Hz), 1.1–1.4 (34H, m), 1.48 (2H, m), 1.85 (2H, quintet, J=7.8 Hz), 2.38 (2H, dd, J=8.3, 7.3 Hz), 2.83 (8H, m), 3.18 (2H, t, J=8.3 Hz), 4.25 (2H, t, J=7.3 Hz), 7.45 (1H, m), 7.66 (1H, d, J=7.8 Hz), 7.74 (1H, m), 8.19 (1H, m), 12.78 (1H, brs).

EXAMPLE 8

2-Heptadecyl-8-methoxy-3-{2-(1-pyrrolidinyl)ethyl}-3-hydroquinazolin-4-one (Compound 8)

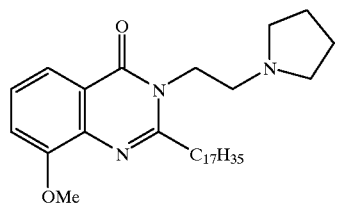

(1) 2-Heptadecyl-8-methoxy-4H-3,1-benzoxazine-4-one

Triethylamine (5.30 ml) was added to a suspension of 2-amino-3-methoxybenzoic acid (3.00 g) in methylene chloride (30 ml). The mixture was cooled with ice and stearoyl chloride (5.44 g) was dropwise added thereto. The reaction mixture was stirred for 2.5 hours at room temperature and then cooled with ice. Then, triethylamine (2.80 ml) and ethyl chlorocarbonate (1.88 ml) were added to the reaction mixture successively. The reaction mixture was stirred for 1 hour at 0° C. and for 3 hours at room temperature successively, and then concentrated. The residue, with chloroform added thereto, was washed with water and saturated brine successively. The organic layer was dried over sodium sulfate anhydride and then concentrated. The residue was purified by silica gel column chromatography (silica gel 150 g, chloroform-hexane), thereby yielding 3.73 g of the aimed compound as colorless solid.

$^1$H-NMR (CDCl$_3$) δ: 0.88 (3H, t, J=6.8 Hz), 1.2–1.5 (28H, m), 1.83 (2H, quintet, J=7.8 Hz), 2.74 (2H, t, J=7.8 Hz), 4.01 (3H, s), 7.27 (1H, dd, J=8.3, 1.5 Hz), 7.43 (1H, t, J=8.3 Hz), 7.78 (1H, dd, J=8.3, 1.5 Hz).

(2) 2-Heptadecyl-8-methoxy-3-{2-(1-pyrrolidinyl)ethyl}-3-hydroquinazolin-4-one 1-(2-Aminoethyl)pyrrolidine (0.88 ml) was added to 2-heptadecyl-8-methoxy-4H-3,1-benzoxazine-4-one (2.62 g). After being stirred for 3 hours at 130° C., the reaction mixture, with ethyl acetate added thereto, was washed with water and saturated brine successively. The organic layer dried over sodium sulfate anhydride, and then concentrated. The residue was purified by silica gel column chromatography (silica gel 75 g, chloroform-methanol), thereby yielding 2.92 g of the aimed compound as colorless solid.

$^1$H-NMR (CDCl$_3$) δ: 0.88 (3H, t, J=6.8 Hz), 1.2–1.4 (26H, m), 1.45 (2H, m), 1.7–1.9 (6H, m), 2.63 (4H, m), 2.78 (2H, t, J=7.8 Hz), 2.92 (2H, t, J=7.8 Hz), 4.00 (3H, s), 4.27 (2H, t, J=7.8 Hz), 7.15 (1H, dd, J=7.8, 1.0 Hz), 7.35 (1H, t, J=7.8 Hz), 7.83 (1H, dd, J=7.8, 1.0 Hz).

EXAMPLE 9

2-Heptadecyl-8-methoxy-3-{2-(1-pyrrolidinyl)ethyl}-3-hydroquinazolin-4-one monohydrochloride (Compound 9)

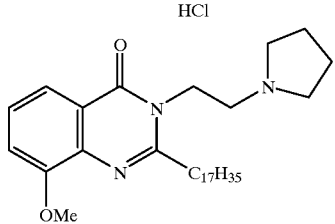

4N hydrochloric acid-ethyl acetate solution (1.36 ml) was dropwise added to a solution of 2-heptadecyl-8-methoxy-3-{2-(1-pyrrolidinyl)ethyl}-3-hydro-quinazolin-4-one (2.51 g) in ethyl acetate (25 ml) while being cooled with ice. After being stirred for 20 minutes at 0° C., the mixture was concentrated. The residue was recrystallized from ethanol-ethyl acetate, thereby yielding 2.18 g of the aimed compound as colorless crystals.

$^1$H-NMR (CDCl$_3$) δ: 0.88 (3H, t, J=6.8 Hz), 1.1–1.4 (26H, m), 1.56 (2H, quintet, J=7.8 Hz), 1.84 (2H, quintet, J=7.8 Hz), 2.12 (2H, m), 2.23 (2H, m), 2.98 (2H, m), 3.07 (2H, t, J=7.8 Hz), 3.33 (2H, m), 3.86 (2H, m), 4.01 (3H, s), 4.73 (2H, t, J=7.8 Hz), 7.20 (1H, dd, J=7.8, 1.0 Hz), 7.39 (1H, t, J=7.8 Hz), 7.76 (1H, dd, J=7.8, 1.0 Hz), 13.24 (1H, brs).

EXAMPLE 10

3-{2-(Diisopropylamino)ethyl}-2-heptadecyl-7-nitro-3-hydroquinazolin-4-one (Compound 10)

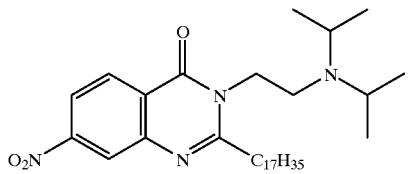

(1) 2-Heptadecyl-7-nitro-4H-3,1-benzoxazine-4-one

Triethylamine (4.85 ml) was added to a suspension of 4-nitroanthranilic acid (3.00 g) in methylene chloride (30 ml) and then the mixture was cooled with ice. The reaction mixture, with stearoyl chloride (4.99 g) dropwise added thereto, was stirred for 3.25 hours at room temperature and then was cooled with ice. Then, triethylamine (2.55 ml) and ethyl chlorocarbonate (1.74 ml) were added to the reaction mixture successively. The reaction mixture was stirred for 1 hour at 0° C. and for 3 hours at room temperature successively, and then concentrated. The residue, with chloroform added thereto, was washed with water and saturated brine successively. The organic layer was dried over sodium sulfate anhydride, and then concentrated. The residue was purified by silica gel column chromatography (silica gel 200 g, chloroform-hexane), thereby yielding 3.62 g of the aimed compound as colorless solid.

$^1$H-NMR (CDCl$_3$) δ: 0.88 (3H, t, J=6.8 Hz), 1.2–1.5 (28H, m), 1.84 (2H, quintet, J=7.6 Hz), 2.73 (2H, t, J=7.6 Hz), 8.27 (1H, dd, J=8.8, 2.0 Hz), 8.37 (1H, d, J=8.8 Hz), 8.40 (1H, d, J=2.0 Hz).

(2) 3-{2-(Diisopropylamino)ethyl}-2-heptadecyl-7-nitro-3-hydroquinazolin-4-one

N,N-Diisopropylethylenediamine (1.16 ml) was added to 2-heptadecyl-7-nitro-4H-3,1-benzoxazine-4-one (2.60 g). After being stirred for 18 hours at 130° C., the reaction mixture, with ethyl acetate added thereto, was washed with water and saturated brine successively. The organic layer dried over sodium sulfate anhydride, and then concentrated. The residue was purified by silica gel column chromatography (silica gel 100 g, chloroform-methanol), thereby yielding 2.96 g of the aimed compound as yellow solid.

$^1$H-NMR (CDCl$_3$) δ: 0.88 (3H, t, J=6.8 Hz), 1.00 (12H, d, J=6.4 Hz), 1.2–1.4 (26H, m), 1.47 (2H, m), 1.85 (2H, quintet, J=7.8 Hz), 2.76 (2H, t, J=6.8 Hz), 2.95 (2H, t, J=7.8 Hz), 3.04 (2H, septet, J=6.4 Hz), 4.08 (2H, t, J=6.8 Hz), 8.17 (1H, dd, J=8.3, 2.0 Hz), 8.39 (1H, d, J=2.0 Hz).

EXAMPLE 11

3-{2-(Diisopropylamino)ethyl}-2-heptadecyl-7-nitro-3-hydroquinazolin-4-one monohydrochloride (Compound 11)

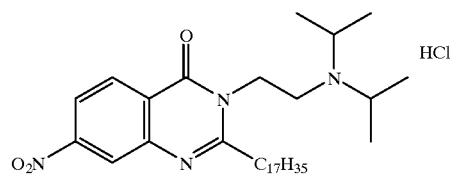

4N hydrochloric acid-ethyl acetate solution (1.20 ml) was dropwise added to a solution of 3-{2-(diisopropylamino)ethyl}-2-heptadecyl-7-nitro-3-hydro-quinazolin-4-one (2.44 g) in ethyl acetate (25 ml) while being cooled with ice. After being stirred for 30 minutes at room temperature, the mixture was concentrated. The residue was recrystallized from ethanol-ethyl acetate, thereby yielding 2.09 g of the aimed compound as light-yellow crystals.

$^1$H-NMR (CDCl$_3$) δ: 0.88 (3H, t, J=6.8 Hz), 1.2–1.4 (26H, m), 1.4–1.6 (8H, m), 1.65 (6H, d, J=6.8 Hz), 1.90 (2H, quintet, J=7.6 Hz), 3.03 (2H, t, J=7.6 Hz), 3.23 (2H, m), 3.77 (2H, m), 4.91 (2H, m), 8.20 (1H, dd, J=8.8, 2.0 Hz), 8.36 (1H, d, J=8.8 Hz), 8.49 (1H, d, J=2.5 Hz), 12.32 (1H, brs).

EXAMPLE 12

7-Amino-3-{2-(diisopropylamino)ethyl}-2-heptadecyl-3-hydroquinazolin-4-one (Compound 12)

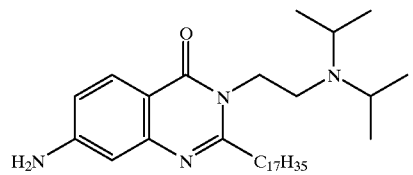

10% Palladium-carbon (105 mg) was added to a solution of 3-{2-(diisopropylamino)ethyl}-2-heptadecyl-7-nitro-3-hydro-quinazolin-4-one (500 mg) in ethyl acetate (5 ml). After being stirred for 2.5 hour at room temperature under hydrogen atmosphere, the reaction mixture was filtrated through Celite™. The filtrate was concentrated, thereby yielding 467 mg of the aimed compound as orange solid.

$^1$H-NMR (CDCl$_3$) δ: 0.88 (3H, t, J=6.8 Hz), 1.03 (12H, d, J=6.8 Hz), 1.2–1.4 (26H, m), 1.44 (2H, m), 1.63 (2H, quintet, J=7.8 Hz), 2.71 (2H, t, J=7.3 Hz), 2.85 (2H, t, J=7.8

Hz), 3.04 (2H, septet, J=6.8 Hz), 4.01 (2H, t, J=7.3 Hz), 4.13 (2H, s), 6.72 (1H, dd, J=8.3, 2.0 Hz), 6.73 (1H, d, J=2.0 Hz), 8.03 (1H, d, J=8.3 Hz).

EXAMPLE 13

7-Amino-3-{2-(Diisopropylamino)ethyl}-2-heptadecyl-3-hydroquinazolin-4-one monohydrochloride (Compound 13)

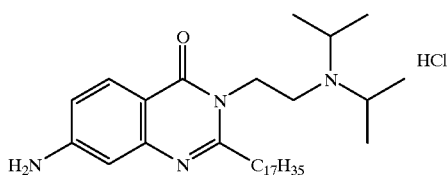

4N hydrochloric acidethyl acetate solution (0.23 ml) was dropwise added to a solution of 7-amino-3-{2-(diisopropylamino)ethyl}-2-heptadecyl-3-hydroquinazolin-4-one (455 mg) in ethyl acetate (5 ml) while being cooled with ice. After being stirred for 20 minutes at 0° C., the mixture was concentrated. The residue was recrystallized from ethanol-ethyl acetate, thereby yielding 363 mg of the aimed compound as colorless crystals.

$^1$H-NMR (CDCl$_3$) δ: 0.88 (3H, t, J=6.8 Hz), 1.2–1.4 (26H, m), 1.4–1.6 (8H, m), 1.63 (2H, d, J=6.3 Hz), 1.85 (2H, quintet, J=7.8 Hz), 2.91 (2H, t, J=7.8 Hz), 3.20 (2H, m), 3.74 (2H, m), 4.27 (2H, s), 4.79 (2H, m), 6.75 (1H, dd, J=8.3, 2.0 Hz), 6.77 (1H, d, J=2.0 Hz), 7.97 (1H, d, J=8.3 Hz), 12.10 (1H, brs).

EXAMPLE 14

3-Decyl-2-{3-(dibutylamino)propyl}-3-hydroquinazolin-4-one (Compound 14)

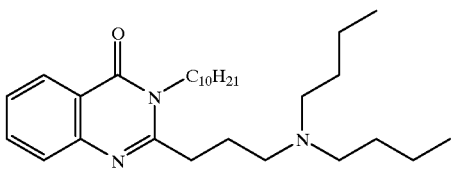

(1) 2-(3-Chloropropyl)-4H-3,1-benzoxazine-4-one

Triethylamine (7.60 ml) was added to a suspension of anthranilic acid (3.52 g) in methylene chloride (35 ml) and then the mixture was cooled with ice. The mixture, with 4-chlorobutyryl chloride (3.62 g) dropwise added thereto, was stirred for 3 hours at room temperature and then cooled with ice. The reaction mixture, with triethylamine (4.00 ml) and ethyl chlorocarbonate (2.70 ml) dropwise added thereto, was stirred for 1 hour at 0° C. and further for 3 hours at room temperature. The reaction mixture, with chloroform added thereto, was washed with water and saturated brine successively. The organic layer was dried over sodium sulfate anhydride and then concentrated. The residue was purified by silica gel column chromatography (silica gel 125 g, chloroform-hexane), thereby yielding 4.00 g of the aimed compound as yellow solid.

$^1$H-NMR (CDCl$_3$) δ: 2.32 (2H, dt, J=7.3, 6.3 Hz), 2.89 (2H, t, J=7.3 Hz), 3.71 (2H, t, J=6.3 Hz), 7.51 (1H, dd, J=8.3, 7.8 Hz), 7.57 (1H, d, J=8.3 Hz), 7.80 (1H, ddd, J=8.3, 7.8, 1.5 Hz), 8.20 (1H, dd, J=7.8, 1.5 Hz).

(2) 2-{(4-Chlorobutanoyl)amino}-N-decylbenzamide n-Decylamine (0.45 ml) was added to 2-(3-chloropropyl)-4H-3,1-benzoxazine-4-one (0.50 g). After being stirred for 45 minutes at 40° C., the reaction mixture was purified by silica gel column chromatography (silica gel 50 g, chloroform), thereby yielding 0.59 g of the aimed compound as light-yellow solid.

$^1$H-NMR (CDCl$_3$) δ: 0.88 (3H, t, J=6.8 Hz), 1.2–1.5 (14H, m), 1.63 (2H, m), 2.20 (2H, dt, J=7.3, 6.3 Hz), 2.60 (2H, t, J=7.3 Hz), 3.43 (2H, q, J=6.6 Hz), 3.65 (2H, t, J=6.3 Hz), 6.22 (1H, m), 7.07 (1H, td, J=7.8, 1.0 Hz), 7.4–7.5 (2H, m), 8.58 (1H, d, J=8.3 Hz), 11.15 (1H, brs).

(3) 3-Decyl-2-{3-(dibutylamino)propyl}-3-hydroquinazolin-4-one

Di-n-butylamine (0.26 ml) was added to 2-{(4-chlorobutanoyl)Amino}-N-decyl benzamide (0.29 g). The mixture was stirred for 1.5 hours at 50° C., for 90 hours at 70° C., and for 22 hours at 130° C. successively. The reaction mixture, with ethyl acetate added thereto, was washed with saturated sodium hydrogencarbonate aqueous solution and saturated brine successively. The organic layer was dried over sodium sulfate anhydride and then concentrated. The residue was purified by silica gel column chromatography (silica gel 20 g, chloroform-methanol), thereby yielding 33 mg of brown oil containing the aimed compound. The typical chemical shifts due to the aimed compound is shown below.

$^1$H-NMR (CDCl$_3$) δ: 2.87 (2H, t, J=7.3 Hz), 4.09 (2H, t, J=7.8 Hz), 7.60 (1H, d J=7.8 Hz), 7.70 (1H, m), 8.24 (1H, d, J=7.8 Hz).

| Compounding Example 1 Hair growth tonic | |
|---|---|
| Quinazolinone derivative (Compound 4) | 0.5 wt % |
| Pyridoxine dioctanoate | 0.1 |
| Pantothenyl ethylether | 0.2 |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |
| <Preparation Method> | |

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 2 Hair regrowth promoting liquid lotion | |
|---|---|
| Quinazolinone derivative (Compound 1) | 0.2 wt % |
| Carpronium chloride | 1.0 |
| Pantothenyl ethylether | 0.5 |
| Diphenhydramine hydrochloride | 0.1 |
| Hinokitiol | 0.1 |
| dl-α-tocopheryl acetate | 0.1 |
| Salicylic acid | 0.2 |
| 1-Menthol | 0.2 |
| Glycyrrhizinic acid | 0.1 |
| Sodium dl-pyrrolidonecarboxylate solution | 1.0 |
| Ethanol | 70.0 |
| Purified water | Balance |
| <Preparation Method> | |

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 3 Hair tonic | |
|---|---|
| Quinazolinone derivative (Compound 2) | 0.1 wt % |
| Paeony root extract (1,3-butylene glycol extract) | 0.01 |
| N,N-dihydroxymethyl-2-tetraeiocylamineoxide | 1.0 |
| N,N-dimethyl-2-decyltetradecylamineoxide | 1.0 |
| Hinokitiol | 1.0 |
| Vitamin $B_6$ | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10 mol) monostearate | 2.0 |
| 75% Ethanol | Balance |
| <Preparation Method> | |

Each of the above ingredients was added and dissolved into 75% ethanol successively with stirring to obtain a hair tonic.

| Compounding Example 4 Hair tonic | |
|---|---|
| Paeonia extract (ethanol extract) | 5.0 wt % |
| Quinazolinone derivative (Compound 2) | 0.05 |
| Quinazolinone derivative (Compound 7) | 0.05 |
| Hinokitiol | 1.0 |
| Vitamin $B_6$ | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |
| <Preparation Method> | |

Each of the above ingredients was added and dissolved into 75% ethanol successively with stirring to obtain a hair tonic.

| Compounding Example 5 Hair tonic | |
|---|---|
| Quinazolinone derivative (Compound 1) | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-dimethyl-2-decyltetradecylamineoxide | 0.5 |
| N,N-dihydroxymethyl-2-hyxadecylamineoxide | 0.5 |
| Dimethylhexyl polyoxyethylene (5 mol) aminoexide | 0.5 |
| Polyoxyethylene (40) hydrogenated castor Oil | 0.5 |
| Succinic acid | Q.S. |
| Perfume and coloring agent | Q.S. |
| Purified water | Balance |
| <Preparation Method> | |

A hair tonic was prepared according to Compounding Example 1.

| Compounding Example 6 Hair lotion | |
|---|---|
| 95% Ethanol | 90.0 wt % |
| Vitamin E acetate | 0.05 |
| Quinazolinone derivative (Compound 2) | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |
| <Preparation Method> | |

Polyoxyethylene (40) hydrogenated castor oil and perfume were dissolved in 95% ethanol. Then, purified water and the other ingredients were added and dissolved into the mixture successively with stirring to obtain a transparent liquid lotion.

| Compounding Example 7 Hair tonic | |
|---|---|
| Quinazolinone derivative (Compound 7) | 0.1 wt % |
| Hinokitiol | 1.0 |
| Vitamin $B_6$ | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |
| <Preparation Method> | |

Each of the above ingredients was added and dissolved into 75% ethanol successively with stirring to obtain a hair tonic.

| Compounding Example 8 Hair tonic | |
|---|---|
| Quinazolinone derivative (Compound 2) | 0.5 wt % |
| Quinazolinone derivative (Compound 7) | 0.1 |
| Hinokitiol | 1.0 |
| Vitamin $B_6$ | 0.2 |
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10 mol) monostearate | 2.0 |
| 70% Ethanol | Balance |
| <Preparation Method> | |

Each of the above ingredients was added and dissolved into 70% ethanol successively with stirring to obtain a hair tonic.

| Compounding Example 9 O/W type milky lotion | |
|---|---|
| (Phase A) | |
| Polyoxyethylene (60) hydrogenated castor oil | 2.0 wt % |
| Glycerin | 10.0 |
| Dipropylene glycol | 10.0 |
| 1,3-Butylene glycol | 4.0 |

Compounding Example 9 O/W type milky lotion

| | |
|---|---|
| Quinazolinone derivative (Compound 1) | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinylpolymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |
| <Preparation Method> | |

Phases A and B were heated and dissolved, separately. Both were mixed and treated with a homomixer, thereby obtaining a gel. Phase D was then gradually added to this gel and dispersed by the homomixer. Then, Phases C and E were added to this gel dispersion successively, which were mixed and dissolved in advance separately. The mixture was emulsified by the homomixer to obtain an O/W type milky lotion.

Compounding Example 10 Cream

| | |
|---|---|
| (Phase A) | |
| Dimethylhexylpolyoxyethylene (5 mol) amineoxide | 2.5 wt % |
| Liquid paraffin | 5.0 |
| Cetostearyl alcohol | 5.5 |
| Glyceryl monostealate | 3.0 |
| Polyoxydylene (20) 2-octyldodecyl ether | 3.0 |
| Propyl paraben | 0.3 |
| Perfume | 0.1 |
| (Phase B) | |
| Quinazolinone derivative (Compound 2) | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |
| <Preparation Method> | |

Phases A and B were heated and dissolved, separately. Both were mixed and emulsified by a homomixer to obtain a cream.

Compounding Example 11 Aerosol spray

| | |
|---|---|
| (Stock solution) | |
| 95% Ethanol | 50.0 wt % |
| Glycyrrhizic acid | 0.1 |
| Quinazolinone derivative (Compound 7) | 0.5 |
| Swertia herb extract | 0.1 |
| Sodium lauryl sulfate | 0.1 |
| Polyoxyethylene (40) hydrogenated castor oil | 0.5 |
| Lactic acid | Q.S. |
| Sodium lactate | Q.S. |
| Perfume | Q.S. |
| Ion-exchanged water | Balance |

Compounding Example 11 Aerosol spray

| | |
|---|---|
| (Filling formulation) | |
| Stock solution | 50.0 |
| Liquefied petroleum gas | 50.0 |
| <Preparation Method> | |

A stock solution was prepared by mixing and dissolving the ingredients of stock solution. This stock solution was filled into a can and a valve was fit thereto. Liquefied petroleum gas was filled into the can to obtain an aerosol spray.

Compounding Example 12 Shampoo

| | |
|---|---|
| (1) Sodium cocoylmethyl taurate | 2.0 wt % |
| (2) Polyoxyethylene (8) oleylether | 2.0 |
| (3) Lauric acid diethanolamide | 4.0 |
| (4) Ethylene glycol fatty acid ester | 1.0 |
| (5) Glycerine | 0.2 |
| (6) Menthol | 0.1 |
| (7) Quinazolinone derivative (Compound 1) | 0.1 |
| (8) Disodium edetate | 0.1 |
| (9) Perfume | Q.S. |
| (10) Purified water | Balance |
| <Preparation Method> | |

The ingredient (10) was heated up to 70° C. The ingredients (1)–(9) were added to the heated ingredient (10) successively and the mixture was mixed and dissolved with stirring. The mixture was cooled to obtain a shampoo.

Compounding Example 13 Rinse

| | |
|---|---|
| (1) Stearyl trimethyl ammonium chloride | 1.5 wt % |
| (2) Dimethyl polysiloxane (20 cs) | 3.0 |
| (3) Polyoxyethylene (10) oleylether | 1.0 |
| (4) Glycerine | 5.0 |
| (5) Quinazolinone derivative (Compound 2) | 0.5 |
| (6) 4-Tert-butyl-4'-methoxydibenzoylmethane | Q.S. |
| (7) Ultraviolet absorber | Q.S. |
| (8) Purified water | Balance |
| <Preparation Method> | |

The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

Compounding Example 14 Scalp treatment

| | |
|---|---|
| (Stock solution) | |
| (1) Liquid paraffin | 27.0 wt % |
| (2) Stearic acid | 5.0 |
| (3) Cetanol | 5.0 |
| (4) Sorbitan monooleate | 2.0 |
| (5) Polyoxyethylene sorbitan monooleate | 3.0 |
| (6) Quinazolinone derivative (Compound 7) | 0.1 |
| (7) 1,3-Butylene glycol | 5.0 |
| (8) Antiseptic | Q.S. |
| (9) Purified water | Balance |

-continued

Compounding Example 14
Scalp treatment (Stock solution)
(Filling formulation)

| | |
|---|---|
| Stock solution | 50.0 |
| Liquefied petroleum gas | 50.0 |

<Preparation Method>

The ingredients (5) and (6) were dissolved into ingredients (1) to (4). After being dissolved with heating up to 80° C., the mixture was cooled down. This mixture was added to the mixed solution of the ingredients (7) to (9), which was maintained at 30° C., and mixed with stirring to obtain a stock solution. This stock solution was filled into a can together with a propellant to obtain a scalp treatment.

Compounding Example 15
Scalp treatment (Stock solution)

| | | |
|---|---|---|
| (1) | Hinokitiol | 0.1 wt % |
| (2) | Swertia herb extract | 1.0 |
| (3) | Vitamin $B_6$ | 0.1 |
| (4) | Vitamin E | 0.01 |
| (5) | Menthol | 0.1 |
| (6) | Salicylic acid | 0.001 |
| (7) | Quinazolinone derivative (Compound 2) | 0.1 |
| (8) | Polyoxyethylene sorbitan monooleate | 0.1 |
| (8) | Propylene glycol | 2.0 |
| (10) | 75% Ethanol | Balance |

(Filling formulation)

| | |
|---|---|
| Stock solution | 50.0 |
| Dimethyl ether | 50.0 |

<Preparation Method>

A scalp treatment was prepared according to Compounding Example 14.

In the following, the compounds and manufacturing processes thereof in accordance with the present invention are exemplified.

Compound 15

3-{2-(Dimethylamino)ethyl}-2-heptadecyl-3-hydroquinazolin-4-one

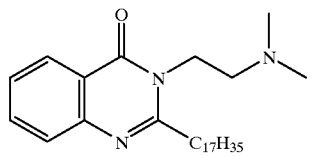

In Example 1–4 (2), N,N-dimethylethylenediamine is used in place of N,N-dimethyl-1,3-propanediamine to obtain the aimed compound.

Compound 16

2-Heptadecyl-3-(3-piperidinopropyl)-3-hydroquinazolin-4-one

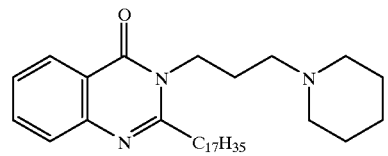

In Example 1–4 (2), 3-piperidinopropylamine is used in place of N,N-dimethyl-1,3-propanediamine to obtain the aimed compound.

Compound 17

3-{3-(Diethylamino)propyl}-2-heptadecyl-3-hydroquinazolin-4-one

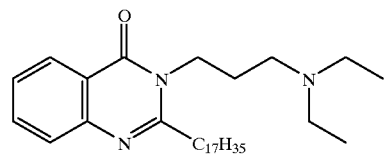

In Example 1–4 (2), N,N-diethyl-1,3-propanediamine is used in place of N,N-dimethyl-1,3-propanediamine to obtain the aimed compound.

Compound 18

3-(3-Aminopropyl)-2-heptadecyl-3-hydroquinazolin-4-one dihydrochloride

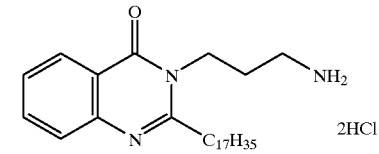

In Example 1–4 (2), tert-butyl N-(3-aminopropyl) carbamate is used in place of N,N-dimethyl-1,3-propanediamine to obtain 3-{3-{N-(tert-butoxycarbonyl)amino}propyl}-2-heptadecyl-3-hydroquinazolinon-4-one.

This compound is deprotected in ethyl acetate by using hydrochloric acid-ethyl acetate, to obtain the aimed compound.

Compound 19

3-{3-(Dimethylamino)propyl}-2-heptadecyl-8-methyl-3-hydroquinazolinon-4-one

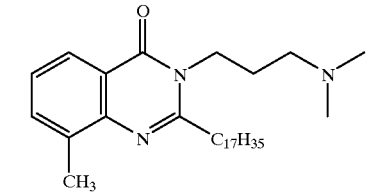

In Example 1–4 (1), 2-amino-3-methylbenzoic acid is used in place of anthranilic acid to obtain 2-heptadecyl-8-methyl-4H-3,1-benzoxazin-4-one.

In the similar manner to Example 1–4 (2), from 2-heptadecyl-8-methyl-4H-3,1-benzoxazin-4-one and N,N-dimethyl-1,3-propanediamine, the aimed compound is obtained.

Compound 20
7-Chloro-3-{-3-(dimethylamino)propyl}-2-heptadecyl-3-hydroquinazolin-4-one

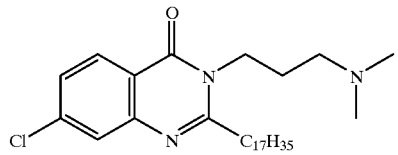

In Example 1–4 (1), 2-amino-4-chlorobenzoic acid is used in place of anthranilic acid to obtain 7-chloro-2-heptadecyl-4H-3,1-benzoxazin-4-one.

In the similar manner to Example 1–4 (2), from 7-chloro-2-heptadecyl-4H-3,1-benzoxazin-4-one and N,N-dimethyl-1,3-propanediamine, the aimed compound is obtained.

Compound 21
3-{2-(Dimethylamino)ethyl}-2-tridecyl-3-hydroquinazolin-4-one

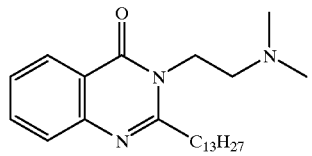

In Example 4 (2), N,N-dimethylethylenediamine is used in place of N,N-dimethyl-1,3-propanediamine to obtain the aimed compound.

Compound 22
3-(3-Piperidinopropyl)-2-tridecyl-3-hydroquinazolinon4-one

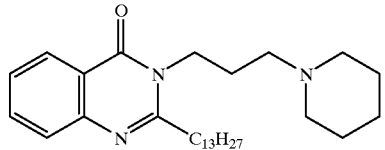

In Example 4 (2), 3-piperidinopropylamine is used in place of N,N-dimethyl-1,3-propanediamine to obtain the aimed compound.

Compound 23
3-(3-Aminopropyl)-2-tridecyl-3-hydroquinazolin-4-one dihydrochloride

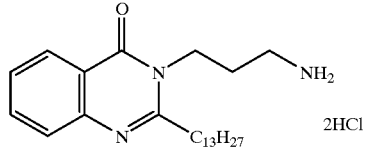

In Example 4 (2), tert-butyl N-(3-aminopropyl)carbamate is used in place of N,N-dimethyl-1,3-propanediamine to obtain 3-{3-{N-(tert-butoxycarbonyl)amino}propyl}-2-tridecyl-3-hydroquinazolin-4-one.

This compound is deprotected in ethyl acetate by using hydrochloric acid-ethyl acetate, to obtain the aimed compound.

Compound 24
2-{3-(Dimethylamino)propyl}-3-octadecyl-3-hydroquinazolin-4-one

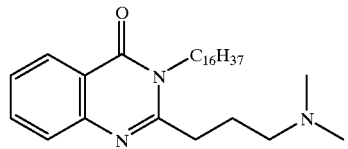

In Example 14 (2), 1-octadecylamine is used in place of n-decylamine to obtain 2-{(4-chlorobutanoyl)amino}-N-octadecylbenzamide.

In the similar manner to Example 14 (3), from 2-{(4-chlorobutanoyl)amino}-N-octadecylbenzamide and dimethylamine hydrochloride, the aimed compound is obtained.

Compound 25
3-Octadecyl-2-(3-piperidinopropyl)-3-hydroquinazolin-4-one

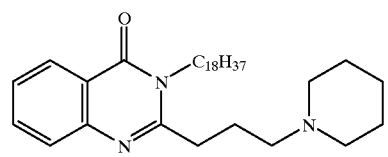

In the similar manner to Example 14 (3), from 2-{(4-chlorobutanoyl)amino}-N-octadecylbenzamide and piperidine, the aimed compound is obtained.

Compound 26
2-(3-Morpholinopropyl)-3-octadecyl-3-hydroquinazolin-4-one

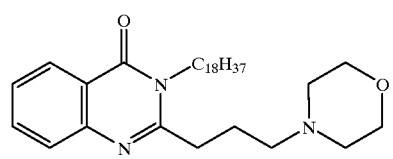

In the similar manner to Example 14 (3), from 2-{(4-chlorobutanoyl)amino}-N-octadecylbenzamide and morpholine, the aimed compound is obtained.

Compound 27
2-{3-(Diethylamino)propyl}-3-octadecyl-3-hydroquinazolin-4-one

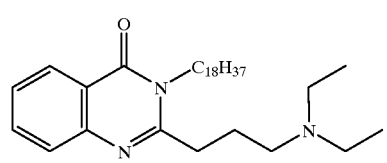

In the similar manner to Example 14 (3), from 2-{(4-chlorobutanoyl)amino}-N-octadecylbenzamide and diethylamine, the aimed compound is obtained.

Compound 28
2-(3-Aminopropyl)-3-octadecyl-3-hydroquinazolin-4-one

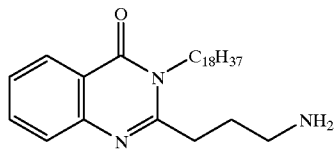

2-{(4-Chlorobutanoyl)amino}-N-octadecylbenzamide and potassium phthalimide are reacted in DMF at 80° C. to obtain 2-{{4-(phthalimide)butanoyl}amino}-N-octadecylbenzamide.

In the similar manner to Example 1–3, 3-octadecyl-2-{3-(phthalimide)propyl}-3-hydroquinazoline-4-one is obtained from 2-{{4-(phthalimide)butanoyl}amino}-N-octadecylbenzamide.

3-Octadecyl-2-{3-(phthalimide)propyl}-3-hydroquinazoline-4-one is reacted with hydrazine in ethanol at reflux temperature to obtain the aimed compound.

Compound 29

2-{3-(Dimethylamino)propyl}-3-tetradecyl-3-hydroquinazolin-4-one

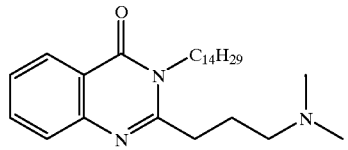

In Example 14 (2), 1-tetradecylamine is used in place of n-decylamine to obtain 2-{(4-chlorobutanoyl)amino}-N-tetradecylbenzamide.

In the similar manner to Example 14 (3), from 2-{(4chlorobutanoyl)amino}-N-tetradecylbenzamide and dimethylamine hydrochloride, the aimed compound is obtained.

Compound 30

2-{3-(Diethylamino)propyl}-3-tetradecyl-3-hydroquinazolin-4-one

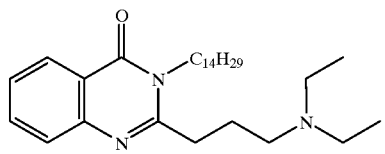

In the similar manner to Example 14 (3), from 2-{(4-chlorobutanoyl)amino}-N-tetradecylbenzamide and diethylamine, the aimed compound is obtained.

Compound 31

2-(3-Aminopropyl)-3-tetradecyl-3-hydroquinazolin-4-one

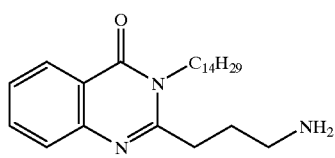

2-{(4-Chlorobutanoyl)amino}-N-tetradecylbenzamide and potassium phthalimide are reacted in DMF at 80° C. to obtain 2-{{4-(phthalimide)butanoyl}amino}-N-tetradecylbenzamide.

In the similar manner to Example 1–3, 3-tetradecyl-2-{3-(phthalimide)propyl}-3-hydroquinazoline-4-one is obtained from 2-{{4-phthalimide)butanoyl}amino}-N-tatradecylbenzamide.

3-Tetradecyl-2-{3-(phthalimide)propyl}-3-hydroquinazolinone is reacted with hydrazine in ethanol at reflux temperature to obtain the aimed compound.

Also, the following compounds should be included in the category of the present invention.

Compound 32

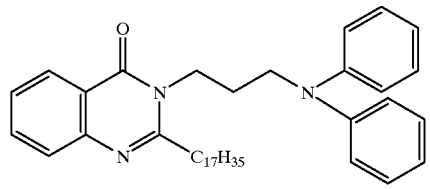

Compound 33

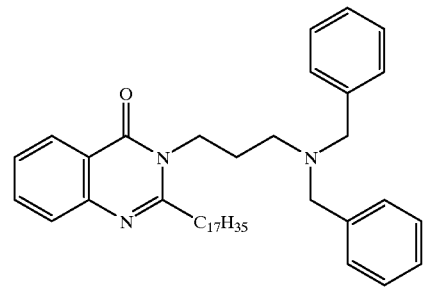

Compound 34

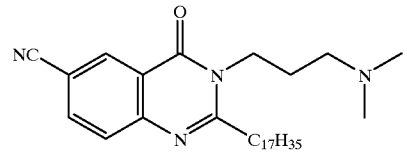

Compound 35

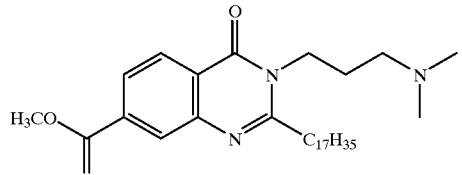

Compound 36

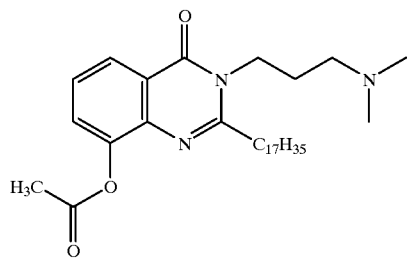

Compound 37

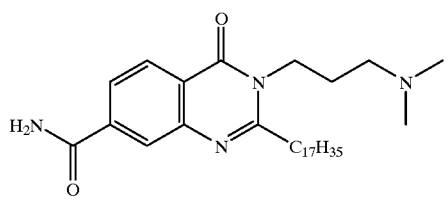

Compound 38

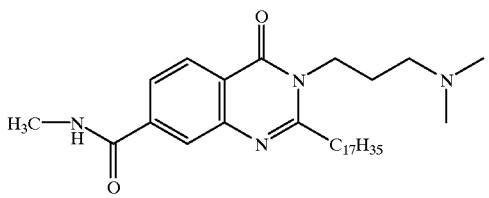

Compound 39

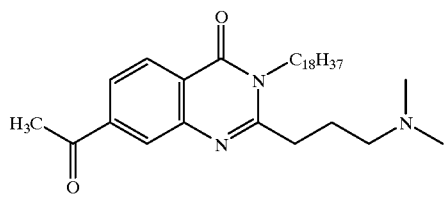

Compound 40

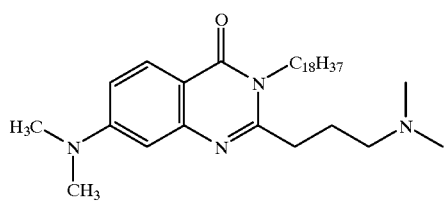

Compound 41

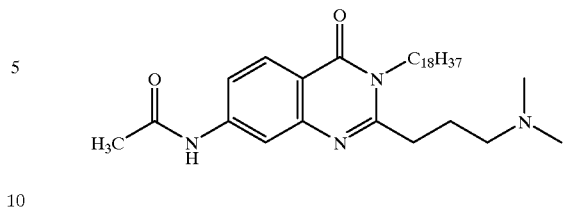

What is claimed is:

1. A quinazolinone derivative or a salt thereof expressed by the following Formula (I):

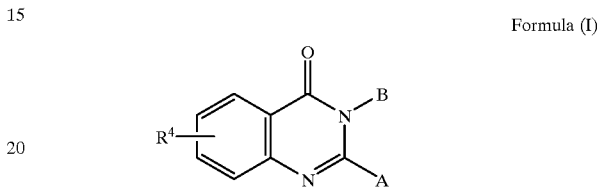

Formula (I)

wherein each of A and B is $R^1$ or $-(CH_2)_n-NR^2R^3$;
wherein $R^1$ represents a hydrocarbon group of $C_{10-30}$;
wherein $R^2$ and $R^3$ individually represent a hydrogen atom, a lower alkyl group, a phenyl group, or a benzyl group, or wherein $-NR^2R^3$ represents a heterocyclic ring having 3–7 members;
wherein said heterocyclic ring is unsubstituted or substituted; and n represents an integer of 1–5;
wherein when A is $R^1$, B is $-(CH_2)_n-NR^2R^3$ and when A is $-(CH_2)_n-NR^2R^3$, B is $R^1$; and
wherein $R^4$ is selected from the group consisting of a hydrogen atom, a halogen atom, a lower alkyl group, a lower acyl group, a nitro group, a cyano group, an amino group, a lower alkoxycarbonyl group, a lower alkylamino group, a lower alkoxy group, a lower acyloxy group, a carbamoyl group, a lower alkylcarbamoyl group, and a lower acylamino group, wherein said lower acyl group is straight or branched acyl group having 2–7 carbon atoms.

2. A quinazolinone derivative or a salt thereof according to claim 1, wherein A is $R^1$ and B is $-(CH_2)_n-NR^2R^3$.

3. A quinazolinone derivative or a salt thereof according to claim 1, wherein $R^1$ is an alkyl group of $C_{10-30}$.

4. A quinazolinone derivative or a salt thereof according to claim 1, wherein n is 2 or 3.

5. A quinazolinone derivative or a salt thereof according to claim 1, wherein A is $-(CH_2)_n-NR^2R^3$ and B is $R^1$.

6. A hair growth promoting composition comprising an effective amount of the quinazolinone derivative or the pharmacologically acceptable salt thereof according to claim 1 and a pharmacologically acceptable carrier.

7. A method for promoting hair growth, which comprises applying an effective amount of the quinazolinone derivative or the pharmacologically acceptable salt thereof according to claim 1 on skin of mammals.

8. A method for promoting hair growth according to claim 7, wherein the skin of mammals is human scalp.

9. The quinazolinone derivative according to claim 1, wherein said heterocyclic ring further comprises an oxygen atom.

10. The quinazolinone derivative according to claim 1, wherein said unsubstituted heterocyclic ring is selected from the group consisting of aziridine, azetidine, pyrrolidine, piperidine, homopiperidine, piperazine, morpholine, pyrrole, pyrazole, and imidazole ring.

11. The quinazolinone derivative according to claim 1, wherein said substituted heterocyclic ring is substituted by one or two substituents selected from the group consisting of a lower alkyl, a lower alkoxy, a lower acyl and a nitro group.

12. The quinazolinone derivative according to claim 1, wherein said lower acyl group is selected from the group consisting of acetyl, propionyl, butyryl, isobutyryl, pivaloyl, and benzoyl group.

* * * * *